United States Patent
Park et al.

(10) Patent No.: US 10,927,097 B2
(45) Date of Patent: Feb. 23, 2021

(54) INDOLE COMPOUND AS INHIBITOR OF NECROSIS

(71) Applicant: LG CHEM, LTD., Seoul (KR)

(72) Inventors: Heui Sul Park, Deajeon (KR); Sun Young Koo, Daejeon (KR); Hyoung Jin Kim, Daejeon (KR); Sung Bae Lee, Daejeon (KR); Hyo Shin Kwak, Daejeon (KR); Vasily Artemov, Daejeon (KR); Soon Ha Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 301 days.

(21) Appl. No.: 14/913,132

(22) PCT Filed: Aug. 21, 2014

(86) PCT No.: PCT/KR2014/007758
§ 371 (c)(1),
(2) Date: Feb. 19, 2016

(87) PCT Pub. No.: WO2015/026170
PCT Pub. Date: Feb. 26, 2015

(65) Prior Publication Data
US 2016/0200709 A1    Jul. 14, 2016

(30) Foreign Application Priority Data

Aug. 22, 2013   (KR) ......................... 10-2013-0099960

(51) Int. Cl.
| | | |
|---|---|---|
| *C07D 403/06* | (2006.01) | |
| *C07D 403/12* | (2006.01) | |
| *C07D 403/14* | (2006.01) | |
| *C07D 401/14* | (2006.01) | |
| *C07D 417/06* | (2006.01) | |
| *C07D 417/14* | (2006.01) | |
| *C07D 487/04* | (2006.01) | |
| *C07D 209/12* | (2006.01) | |
| *C07D 209/14* | (2006.01) | |
| *C07D 401/04* | (2006.01) | |
| *C07D 403/04* | (2006.01) | |
| *C07D 209/08* | (2006.01) | |

(52) U.S. Cl.
CPC ......... *C07D 403/06* (2013.01); *C07D 209/08* (2013.01); *C07D 209/12* (2013.01); *C07D 209/14* (2013.01); *C07D 401/04* (2013.01); *C07D 401/14* (2013.01); *C07D 403/04* (2013.01); *C07D 403/12* (2013.01); *C07D 403/14* (2013.01); *C07D 417/06* (2013.01); *C07D 417/14* (2013.01); *C07D 487/04* (2013.01)

(58) Field of Classification Search
CPC .. C07D 403/06; C07D 403/14; C07D 403/12; C07D 403/04; C07D 401/04; C07D 401/14; C07D 417/06; C07D 417/14; C07D 487/04; C07D 209/08; C07D 209/12; C07D 209/14
USPC .............. 514/254.02, 415, 515; 544/367; 548/491, 362.5, 490
See application file for complete search history.

(56) References Cited

U.S. PATENT DOCUMENTS

| | | | | |
|---|---|---|---|---|
| 2010/0197673 | A1* | 8/2010 | Kim ..................... | C07D 413/04 514/228.2 |
| 2010/0291533 | A1* | 11/2010 | Kim ..................... | C07D 209/08 435/1.1 |
| 2012/0270203 | A1 | 10/2012 | Kim et al. | |
| 2014/0024618 | A1 | 1/2014 | Kim et al. | |

FOREIGN PATENT DOCUMENTS

| | | |
|---|---|---|
| KR | 10-2009-0018593 A | 2/2009 |
| KR | 10-2009-0018594 A | 2/2009 |
| KR | 10-2009-0075638 A | 7/2009 |
| KR | 10-2013-0087283 A | 8/2013 |
| WO | WO 95/07276 A1 | 3/1995 |
| WO | WO 2004/018428 A1 | 3/2004 |

(Continued)

OTHER PUBLICATIONS

International Search Report, issued in PCT/KR2014/007758, dated Nov. 28, 2014.
Kreamer, B.L. et al, "Use of a Low-Speed Iso-Density Percoll Centrifugation Method to Increase the Viability of Isolated Rat Hepatocyte Preparations," In Vitro Cellular & Development Biology, Apr. 1986, vol. 22, No. 4, pp. 201-211.
Proskuryakov, S.Y. et al, "Necrosis Is an Active and Controlled Form of Programmed Cell Death," Biochemistry (Moscow), 2002, vol. 67, No. 4, pp. 387-408.
Seglen, P.O., "Preparation of Rat Liver Cells," Experimental Cell Research, 1972, vol. 74, pp. 450-454.

(Continued)

Primary Examiner — Irina Neagu
(74) Attorney, Agent, or Firm — Birch, Stewart, Kolasch & Birch, LLP

(57) ABSTRACT

The present application relates to an indole compound represented by formula (1):

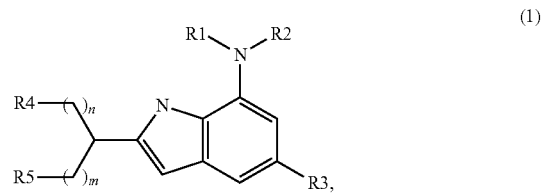

(1)

a pharmaceutically acceptable salt or isomer thereof, a composition for prevention or treatment of necrosis and necrosis-associated diseases, and a method for preparing the composition, the composition comprising the indole compound or the pharmaceutically acceptable salt or isomer thereof as an active ingredient.

16 Claims, No Drawings

(56) References Cited

FOREIGN PATENT DOCUMENTS

WO    WO 2006/0112549 A1    10/2006

OTHER PUBLICATIONS

Brunt et al, "Nonalcoholic Steatohepatitis: A Proposal for Grading and Staging the Histological Lesions," The American Journal of Gastroenterology, vol. 94, No. 9, Sep. 1999, pp. 2467-2474.
CHEMCATS CAS Registry No. 910442-88-5, Database Registry [Online], dated Oct. 15, 2006, 1 Page.
Matteoni et al, "Nonalcoholic Fatty Liver Disease: A Spectrum of Clinical and Pathological Severity," Gastroenterology, vol. 116, No. 6, Jun. 1999, pp. 1413-1419.
Neuschwander-Tetri et al, "Nonalcoholic Steatohepatitis: Summary of an AASLD Single Topic Conference," Hepatology, vol. 37, No. 5, May 2003, p. 1202-1219.

\* cited by examiner

INDOLE COMPOUND AS INHIBITOR OF NECROSIS

The instant application is a National Stage entry of International Application No. PCT/KR2014/007758, filed on Aug. 21, 2014, which claims priority from Korean Patent Application No. 10-2013-0099960, filed on Aug. 22, 2013.

TECHNICAL FIELD

The present invention relates to an indole compound of Formula (1), a pharmaceutically acceptable salt or isomer thereof, and a composition and a method of preparing a composition for the prevention or treatment of cellular necrosis and necrosis-associated diseases comprising the same as an active ingredient.

BACKGROUND ART

Most researches associated with cell death have been focused on apoptosis of cells, also known as programmed cell death (PCD). With the discovery of the enzyme caspase, a number of pharmaceutical companies have promoted the development of drugs utilizing caspase inhibitors during the past 10 years. However, the current status is that no drug has been approved by the FDA. This is because the apoptosis of cells is a cell death which occurs under physiological circumstances, and such a cell death may be due to the defense mechanism for maintaining homeostasis in the body. In contrast, necrosis is a cell death which mainly occurs under pathologic circumstances, and in most cases it is characterized by an accompanying inflammatory response. Necrosis has been known as an uncontrolled cell death for a long time, but according to recent research (Proskurykakov S Y et al., 2002, Biochemistry) typical diseases caused by necrosis include ischemic (e.g., myocardial infarction, stroke, renal infarction), neurodegenerative and inflammatory diseases. Since it is believed that necrosis is an uncontrolled, accidental cell death under pathologic circumstances, researches on the functional mechanism, molecular targets, signal transduction systems, etc. thereof have rarely been conducted. Therefore, there arises a compelling need to discover and develop necrosis-inhibiting substances for the treatment of ischemic, neurodegenerative, and inflammatory diseases which are caused by necrosis, and to elucidate biological, pathological causes of necrosis.

The indole derivatives according to the present invention have very useful structures from a medical viewpoint, and many publications have reported the research results with reference to these structures. Among the research results, the following are the most representative: International Publication No. WO 2006/112549 reported some indole derivatives having activity for glucokinase, International Publication No. WO 95/07276 reported indole derivatives useful as anti-tumor agents and as inhibitors against the production of cardiovascular system, and International Publication No. WO 2004/018428 reported indole derivatives useful as antibiotics.

DISCLOSURE OF INVENTION

Technical Problem

Accordingly, the present inventors have extensively studied under the above-mentioned technical background to develop new compounds that exhibit an effect of prevention or treatment and amelioration of cellular necrosis and necrosis-associated diseases, and are particularly useful for the prevention or treatment of hepatic diseases. As a result thereof, they confirmed that the indole derivatives of Formula (1) as explained below show a superior effect for the prevention and treatment of cellular necrosis and necrosis-associated diseases, whereby they completed the present invention.

Therefore, it is an object of the present invention to provide a novel indole compound of Formula (1), a pharmaceutically acceptable salt or isomer thereof.

It is another object of the present invention to provide a composition for the prevention or treatment of cellular necrosis and necrosis-associated diseases, in particular, for hepatoprotection, hepatic functional improvement, and prevention or treatment of acute/chronic hepatic diseases, which comprises as an active ingredient the compound of Formula (1), a pharmaceutically acceptable salt or isomer thereof together with a pharmaceutically acceptable carrier or diluent.

It is still another object of the present invention to provide a method for the prevention or treatment of cellular necrosis and necrosis-associated diseases, in particular, for hepatoprotection, hepatic functional improvement, and prevention or treatment of acute/chronic hepatic diseases using said composition.

Solution to Problem

To accomplish the above objects, the present invention provides an indole compound of the following Formula (1) or a pharmaceutically acceptable salt or isomer thereof:

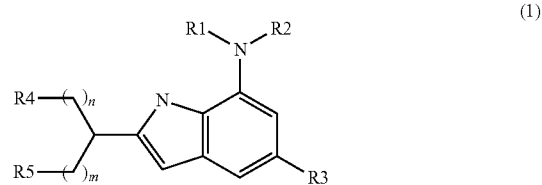

(1)

in which m denotes a number of 1 to 3, n denotes a number of 0 to 2,

R1 represents hydrogen, $C_1$-$C_6$-alkyl, —$(CH_2)_n$—$C_3$-$C_6$-cycloalkyl or —$(CH_2)_n$-heterocyclyl, wherein heterocyclyl is a 4- to 8-membered ring having 1 to 3 heteroatoms selected from N, O and S, R2 represents $C_1$-$C_6$-alkyl or —$(CH_2)_n$-A-R6, wherein A represents $C_4$-$C_8$-cycloalkyl, or represents 4- to 8-membered heterocyclyl or heteroaryl each of which has 1 to 3 heteroatoms selected from N, O and S, or represents 6- to 10-membered aryl, R6 represents hydrogen, $C_1$-$C_6$-alkyl, halogen, hydroxy, nitrile, nitro, —C(O)—R7 or —$SO_2$R7, and R7 represents $C_1$-$C_6$-alkyl or allyl, or represents 6- to 10-membered aryl, or represents 4- to 8-membered heterocyclyl or heteroaryl each of which has 1 to 3 heteroatoms selected from N and S, and is optionally substituted with oxo, R3 represents hydrogen, halogen, hydroxy, —O—R7, —NH—R7 or —$(CH_2)_n$—R7, R4 represents hydrogen or XR8R9, wherein X represents CH or N, R8 and R9 independently of one another represent hydrogen or Z—R10, Z represents —$(CH_2)_n$—, —C(O)—, —C(O)($CH_2)_n$— or —$(CH_2)_nC(O)$—, R10 represents hydrogen, amino, $C_3$-$C_6$-cycloalkyl or —(NH)$_r$C(=NH)$NH_2$, or represents 4- to 8-membered heteroaryl or heterocyclyl each of which has 1 to 3 heteroatoms selected from N, O and S, and r denotes a number of 0 or 1, R5 represents hydrogen, hydroxy or $C_1$-$C_6$-alkoxy, or represents 6- to 10-membered aryl or 6- to 10-membered aryl-$C_1$-$C_6$-alkyloxy, or represents —$(CH_2)_n$-4- to 9-membered heterocyclyl which has 1 to 4 heteroatoms selected from N, O and S, and optionally contains oxo, R4 and R5 may be connected with an atom(s) to which they are attached to form the following structure:

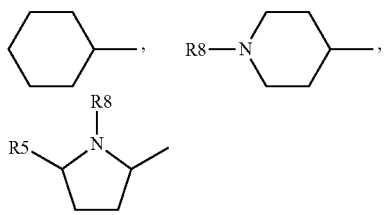

wherein R5 and R8 are the same as defined above, where alkyl, alkoxy, aryl, cycloalkyl, heterocycle and heteroaryl may be optionally substituted, and the substituents are one or more selected from the group consisting of hydroxy, halogen, nitrile, amino, $C_1$-$C_6$-alkylamino, di($C_1$-$C_6$-alkyl)amino, carboxy, $C_1$-$C_6$-alkyl, halogeno-$C_1$-$C_6$-alkyl, $C_1$-$C_6$-alkoxy, aryl-$C_1$-$C_6$-alkoxy and oxo.

In the above definitions for the compound of Formula (1), the term "alkyl" means an aliphatic hydrocarbon radical. Alkyl may be saturated alkyl that does not comprise alkenyl or alkynyl moiety, or unsaturated alkyl that comprises at least one alkenyl or alkynyl moiety. "Alkenyl" means a group containing at least one carbon-carbon double bond, and "alkynyl" means a group containing at least one carbon-carbon triple bond. Alkyl may be branched or straight-chain when used alone or in combination such as alkoxy.

Alkyl group may have 1 to 20 carbon atoms unless otherwise defined. Alkyl group may be a medium-sized alkyl having 1 to 10 carbon atoms. Otherwise, alkyl group may be a lower alkyl having 1 to 6 carbon atoms. Typical examples thereof include, but are not limited to, methyl, ethyl, propyl, isopropyl, n-butyl, isobutyl, t-butyl, pentyl, hexyl, ethenyl, propenyl, butenyl, etc. For example, $C_1$-$C_4$-alkyl has 1 to 4 carbon atoms in the alkyl chain, and is selected from the group consisting of methyl, ethyl, propyl, isopropyl, n-butyl, iso-butyl, sec-butyl and t-butyl.

The term "alkoxy" means an alkyloxy having 1 to 10 carbon atoms unless otherwise defined.

The term "cycloalkyl" means a saturated aliphatic 3- to 10-membered cycle unless otherwise defined. Typical examples thereof include, but are not limited to, cyclopropyl, cyclobutyl, cyclopentyl, cyclohexyl, etc.

The term "aryl" includes at least one ring having covalent π electron system for example, monocyclic or fused polycyclic (i.e., cycles that share the adjacent carbon atom pairs) groups. In the present specification, aryl means an aromatic 4- to 10-membered, preferably 6- to 10-membered, monocyclic or multicyclic ring including phenyl, naphthyl, etc., unless otherwise defined.

The term "heteroaryl" means an aromatic 3- to 10-membered, preferably 4- to 8-membered, more preferably 5- or 6-membered cycle that has 1 to 4 heteroatoms selected from N, O and S, and may be fused with benzo or $C_3$-$C_8$ cycloalkyl, unless otherwise defined. The monocyclic heteroaryl includes, but is not limited to, thiazole, oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine and the like. The bicyclic heteroaryl includes, but is not limited to, indole, indoline, benzothiophene, benzofuran, benzimidazole, benzoxazole, benzisoxazole, benzthiazole, benzthiadiazole, benztriazole, quinoline, isoquinoline, purine, puropyridine and the like.

The term "heterocycle" means a 3- to 10-membered, preferably 4- to 8-membered, more preferably 5- or 6-membered cycle that has 1 to 4 heteroatoms selected from N, O and S, may be fused with benzo or $C_3$-$C_8$ cycloalkyl, and is saturated or contains 1 or 2 double bonds, unless otherwise defined. The heterocycle includes, but is not limited to, pyrroline, pyrrolidine, imidazoline, imidazolidine, pyrazoline, pyrazolidine, pyran, piperidine, morpholine, thiomorpholine, piperazine, hydrofuran and the like.

Other terms and abbreviations in the present specification may be understood to have the meaning conventionally used in this field by a person skilled in the art, unless otherwise defined.

According to a preferred embodiment of the present invention, in the compound of Formula (1):

m denotes a number of 1 to 3, n denotes a number of 0 to 2,

R1 represents hydrogen, $C_1$-$C_6$-alkyl, —$(CH_2)_n$—$C_3$-$C_6$-cycloalkyl or —$(CH_2)_n$-heterocyclyl, wherein heterocyclyl is a 4- to 8-membered ring having 1 to 3 heteroatoms selected from N, O and S, R2 represents $C_1$-$C_6$-alkyl or —$(CH_2)_n$-A-R6, wherein A represents $C_4$-$C_6$-cycloalkyl, or represents 5- or 6-membered heterocyclyl or heteroaryl each of which has 1 to 3 heteroatoms selected from N, O and S, or represents 6- to 10-membered aryl, R6 represents hydrogen, $C_1$-$C_6$-alkyl, halogen, hydroxy, —C(O)—R7 or —$SO_2R7$, and R7 represents $C_1$-$C_6$-alkyl, or represents 6- to 10-membered aryl, or represents 5- or 6-membered heterocyclyl or heteroaryl each of which has 1 to 3 heteroatoms selected from N and S, and is optionally substituted with oxo, R3 represents hydrogen, halogen, —O—R7, —NH—R7 or —$(CH_2)_n$—R7, R4 represents hydrogen or XR8R9, wherein X represents CH or N, R8 and R9 independently of one another represent hydrogen or Z—R10, Z represents —$(CH_2)_n$—, —C(O)—, —C(O)$(CH_2)_n$— or —$(CH_2)_n$C(O)—, R10 represents hydrogen, amino, $C_3$-$C_6$-cycloalkyl or —(NH)$_r$C(=NH)NH$_2$, or represents 4- to 8-membered heteroaryl or heterocyclyl each of which has 1 to 3 heteroatoms selected from N, O and S, and is optionally substituted with amino, and r denotes a number of 0 or 1, R5 represents hydrogen, hydroxy or $C_1$-$C_6$-alkoxy, or represents 6- to 10-membered aryl or 6- to 10-membered aryl-$C_1$-$C_6$-alkyloxy, or represents —$(CH_2)_n$-4- to 9-membered heterocyclyl which has 1 to 4 heteroatoms selected from N, O and S, and optionally contains oxo and is optionally substituted with halogeno-$C_1$-$C_6$-alkyl, R4 and R5 may be connected with an atom(s) to which they are attached to form the following structure:

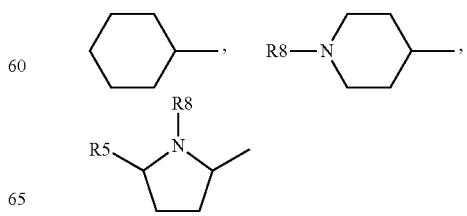

wherein R5 and R8 are the same as defined above.

In the compound of Formula (1) according to the present invention, when R4 is XR8R9, Formula (1) may represent the following Formulas (1a) and (1b) depending on whether R4 and R5 are cyclized or not:

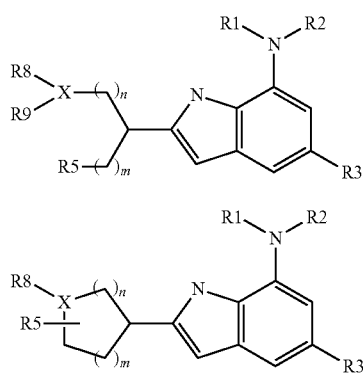

(1a)

(1b)

wherein X, m, n, R1, R2, R3, R5, R8 and R9 are the same as defined above.

Within the scope of the above definitions of m and n, the most preferable structure of the ring of Formula 1b is cyclohexyl, pyrrolidine or piperidine.

Substituent R1 more preferably represents hydrogen or $C_1$-$C_6$-alkyl, or represents 5- or 6-membered heterocyclyl having 1 to 3 heteroatoms selected from N, O and S, and most preferably represents hydrogen, isopentyl or tetrahydropyran.

Substituent R2 more preferably represents $C_1$-$C_6$-alkyl or —$(CH_2)_n$-A-R6, wherein n denotes a number of 0 to 2, A represents $C_4$-$C_6$-cycloalkyl, or represents 5- or 6-membered heterocyclyl having 1 or 2 heteroatoms selected from N and O, or represents phenyl, R6 represents hydrogen, —C(O)—R7 or —$SO_2$R7, R7 represents $C_1$-$C_3$-alkyl. R2 most preferably represents isopentyl, cyclopentyl, benzyl, tetrahydropyran, tetrahydropyran-4-ylmethyl, 1-acetyl-piperidine, tetrahydropyran-2-ylmethyl or piperidin-4-ylmethyl.

Substituent R3 more preferably represents hydrogen, halogen or —$(CH_2)_n$—R7, wherein n denotes a number of 0 to 2, R7 represents $C_1$-$C_6$-alkyl, or represents 5- or 6-membered heterocyclyl which has 1 or 2 heteroatoms selected from N and S, and is optionally substituted with oxo. R3 most preferably represents hydrogen, methyl, chloro or 1,1-dioxothiomorpholin-4-ylmethyl.

Substituent R5 more preferably represents hydrogen, hydroxy or $C_1$-$C_6$-alkoxy, or represents 6- to 10-membered aryl or 6- to 10-membered aryl-$C_1$-$C_3$-alkyloxy, or represents —$(CH_2)_n$-4- to 9-membered heterocyclyl which has 1 to 4 heteroatoms selected from N, O and S, and optionally contains oxo and is optionally substituted with halogeno-$C_1$-$C_3$-alkyl, wherein n denotes a number of 0 to 2. R5 most preferably represents hydrogen, hydroxy, benzyloxy, 1,1-dioxothiomorpholine, 2-oxopiperazine, 3-trifluoromethyl-5,6,7,8-tetrahydro-[1,2,4]triazolo[4,3-a]pyrazin-1-yl, morpholine or phenyl.

Substituent R8 more preferably represents hydrogen or Z—R10, wherein Z represents —$(CH_2)_n$—, —C(O)—, —C(O)$(CH_2)_n$— or —$(CH_2)_n$C(O)—, n denotes a number of 0 to 2, R10 represents hydrogen, amino, $C_4$-$C_6$-cycloalkyl or —$(NH)_rC(=NH)NH_2$, or represents 5- or 6-membered heteroaryl or heterocyclyl each of which has 1 to 3 heteroatoms selected from N and S, and is optionally substituted with amino, r denotes a number of 0 or 1. R8 most preferably represents hydrogen, cyclohexyl-ethyl, 2-amino-pyridin-3-ylmethyl, pyrrolidine, 3-amino-triazol-5-carbonyl, aminomethyl-carbonyl, $NH_2(NH=)C—$, $NH_2(NH=)C—NH—CH_2—C(O)—$, 2-amino-thiazol-4-ylmethyl, cyclopentylmethyl, $NH_2(NH=)C—NH—C(O)—CH_2—$ or acetyl.

Typical compounds of the compound of Formula (1) according to the present invention include the following:
4-(5-Chloro-7-cyclopentylamino-1H-indol-2-ylmethyl)-piperazin-2-one;
4-{2-[5-Chloro-7-(piperidin-4-ylamino)-1H-indol-2-yl]-ethyl}-piperazin-2-one;
4-{2-[7-(1-Acetyl-piperidin-4-ylamino)-5-chloro-1H-indol-2-yl]-ethyl}-piperazin-2-one;
(5-Chloro-7-cyclopentylamino-1H-indol-2-yl)-methanol;
2-(5-Chloro-7-cyclopentylamino-1H-indol-2-yl)-ethanol;
4-{5-Methyl-7-[(piperidin-4-ylmethyl)-amino]-1H-indol-2-ylmethyl}-piperazin-2-one;
[2-(1,1-Dioxothiomorpholin-4-ylmethyl)-5-methyl-1H-indol-7-yl]-(tetrahydropyran-4-ylmethyl)-amine;
Cyclopentyl-[2-(1,1-dioxothiomorpholin-4-ylmethyl)-5-methyl-1H-indol-7-yl]-amine;
4-[5-Methyl-7-(tetrahydropyran-4-ylmethylamino)-1H-indol-2-ylmethyl]-piperazin-2-one;
{5-Chloro-2-[2-(3-trifluoromethyl-5,6,7,8-tetrahydro-[1,2,4]triazolo[4,3-a]pyrazin-1-yl)-ethyl]-1H-indol-7-yl}-(tetrahydrofuran-2-ylmethyl)-amine;
{5-Chloro-2-[2-(3-trifluoromethyl-5,6,7,8-tetrahydro-[1,2,4]triazolo[4,3-a]pyrazin-1-yl)-ethyl]-1H-indol-7-yl}-(tetrahydropyran-2-ylmethyl)-amine;
{5-Chloro-2-[2-(3-trifluoromethyl-5,6,7,8-tetrahydro-[1,2,4]triazolo[4,3-a]pyrazin-1-yl)-ethyl]-1H-indol-7-yl}-(1-methanesulfonyl-piperidin-4-yl)-amine;
1-(4-{5-Chloro-2-[2-(3-trifluoromethyl-5,6,7,8-tetrahydro-[1,2,4]triazolo[4,3-a]pyrazin-1-yl)-ethyl]-1H-indol-7-yl}-piperidin-1-yl)-ethanone;
4-[2-(7-Benzylamino-5-chloro-1H-indol-2-yl)-ethyl]-piperazin-2-one;
4-(2-{5-Chloro-7-[(tetrahydrofuran-2-ylmethyl)-amino]-1H-indol-2-yl}-ethyl)-piperazin-2-one;
4-(2-{5-Chloro-7-[(tetrahydropyran-2-ylmethyl)-amino]-1H-indol-2-yl}-ethyl)-piperazin-2-one;
4-{5-Chloro-7-[(tetrahydropyran-4-ylmethyl)-amino]-1H-indol-2-ylmethyl}-piperazin-2-one;
5-Chloro-2-[2-(1,1-dioxothiomorpholin-4-yl)-ethyl]-1H-indol-7-yl}-(tetrahydropyran-4-yl)-amine;
{5-Chloro-2-[2-(1,1-dioxothiomorpholin-4-yl)-ethyl]-1H-indol-7-yl}-cyclopentyl-amine;
{5-Chloro-2-[2-(3-trifluoromethyl-5,6,7,8-tetrahydro-[1,2,4]triazolo[4,3-a]pyrazin-1-yl)-ethyl]-1H-indol-7-yl}-cyclopentyl-amine;
{5-Chloro-2-[2-(1,1-dioxothiomorpholin-4-yl)-ethyl]-1H-indol-7-yl}-(tetrahydropyran-4-ylmethyl)-amine;
4-(2-{5-Chloro-7-[(tetrahydropyran-4-ylmethyl)-amino]-1H-indol-2-yl}-ethyl)-piperazin-2-one;
{5-Chloro-2-[2-(3-trifluoromethyl-5,6,7,8-tetrahydro-[1,2,4]triazolo[4,3-a]pyrazin-1-yl)-ethyl]-1H-indol-7-yl}-(tetrahydropyran-4-ylmethyl)-amine;
[5-Chloro-2-(2-morpholin-4-yl-ethyl)-1H-indol-7-yl-(tetrahydropyran-4-ylmethyl)-amine;
Cyclopentyl-(5-methyl-2-morpholin-4-ylmethyl-1H-indol-7-yl)-amine;
(2-Cyclohexyl-5-methyl-1H-indol-7-yl)-cyclopentyl-amine:
[2-((R)-1-amino-2-phenyl-ethyl)-5-methyl-1H-indol-7-yl]-cyclopentyl-amine;

{2-[(R)-1-(2-cyclohexyl-ethylamino)-2-phenyl-ethyl]-5-methyl-1H-indol-7-yl}-cyclopentylamine;
Benzyl-{5-chloro-2-[(R)-2-phenyl-1-(pyrrolidin-3-ylamino)-ethyl]-1H-indol-7-yl}-amine;
2-Amino-N—[(R)-1-(7-benzylamino-5-chloro-1H-indol-2-yl)-2-phenylethyl]-acetamide;
N—[(R)-1-(7-Benzylamino-5-chloro-1H-indol-2-yl)-2-phenyl-ethyl]-guanidine;
{2-[(R)-1-(cyclohexylmethyl-amino)-2-phenyl-ethyl]-5-methyl-1H-indol-7-yl}-cyclopentyl-amine;
(2-{(S)-1-[(2-amino-pyridin-3-ylmethyl)-amino]-2-phenyl-ethyl}-5-chloro-1H-indol-7-yl)-(3-methyl-butyl)-amine;
3-Amino-4H-[1,2,4]triazol-4-carboxilic acid [(S)-1-(7-benzylamino-5-chloro-1H-indol-2-yl)-2-phenyl-ethyl]-amide;
2-Amino-N—{(S)-1-[5-chloro-7-(3-methyl-butylamino)-1H-indol-2-yl]-2-phenyl-ethyl}-acetamide;
N—[(R)-1-(7-benzylamino-5-chloro-1H-indol-2-yl)-2-phenyl-ethyl]-2-guanidino-acetamide;
(S)-2-Amino-2-(5-chloro-7-cyclopentylamino-1H-indol-2-yl)-ethanol;
((S)-5-chloro-2-pyrrolidin-2-yl-1H-indol-7-yl)-bis-(3-methyl-butyl)-amine;
(2S,4R)-4-benzyloxy-2-(5-chloro-7-cyclopentylamino-1H-indol-2-yl)-pyrrolidin-1-carboxamidine;
(S)-2-{7-[bis-(3-methyl-butyl)-amino]-5-chloro-1H-indol-2-yl}-pyrrolidin-1-carboxamidine;
(S)-2-(5-chloro-7-cyclopentylamino-1H-indol-2-yl)-pyrrolidin-1-carboxamidine;
[2-((2S,4R)-4-benzyloxy-[1,3']bipyrrolidin-2-yl)-5-chloro-1H-indol-7-yl)-cyclopentyl-amine;
((S)-[1,3']bipyrrolidin-2-yl-5-chloro-1H-indol-7-yl)-cyclopentyl-amine;
{2-[(S)-1-(2-amino-thiazol-4-ylmethyl)-pyrrolidin-2-yl]-5-chloro-1H-indol-7-yl)-cyclopentyl-amine;
[5-Chloro-2-((S)-1-cyclopentylmethyl-pyrrolidin-2-yl)-1H-indol-7-yl]-bis-(3-methyl-butyl)-amine;
((S)-[1,3']bipyrrolidin-2-yl-5-chloro-1H-indol-7-yl)-bis-(3-methyl-butyl)-amine;
N-[2-((S)-2-{7-[bis-(3-methyl-butyl)-amino]-5-chloro-1H-indol-2-yl}pyrrolidin-1-yl)-acetyl]-guanidine;
(5-Chloro-2-piperidin-4-yl-1H-indol-7-yl)-cyclopentyl-amine;
(5-Chloro-2-piperidin-4-yl-1H-indol-7-yl)-(tetrahydropyran-4-yl)-amine;
Cyclopentyl-(5-methyl-2-piperidin-4-yl-1H-indol-7-yl)-amine;
1-[4-(7-Cyclopentylamino-5-methyl-1H-indol-2-yl)-piperidin-1-yl]-ethanone;
(5-Methyl-2-piperidin-4-yl-1H-indol-7-yl)-(tetrahydropyran-4-yl)-amine;
(5-Methyl-2-piperidin-4-yl-1H-indol-7-yl)-bis-(tetrahydropyran-4-yl)-amine;
1-{4-[5-Methyl-7-(tetrahydropyran-4-ylamino)-1H-indol-2-yl]-piperidin-1-yl]-ethanone;
(2-Cyclohexyl-5-methyl-1H-indol-7-yl)-cyclopentyl-amine;
[5-(1,1-Dioxo-thiomorpholin-4-ylmethyl)-2-piperidin-4-yl-1H-indol-7-yl]-(tetrahydropyran-4-yl)-amine; and
1-{4-[5-(1,1-Dioxo-thiomorpholin-4-ylmethyl)-7-(tetrahydropyran-4-ylamino)-1H-indol-2-yl]-piperidin-1-yl}-ethanone.

The compound of Formula (1) according to the present invention can also form a pharmaceutically acceptable salt. Such a "pharmaceutically acceptable salt" includes non-toxic acid addition salt containing pharmaceutically acceptable anion—for example, a salt with inorganic acids such as hydrochloric acid, sulfuric acid, nitric acid, phosphoric acid, hydrobromic acid, hydriodic acid, etc.; a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, naphthalenesulfonic acid, etc. The compound of Formula (1) can also form a pharmaceutically acceptable base addition salt—for example, a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glucamine, tris(hydroxymethyl)methylamine, diethanolamine, choline, triethylamine, etc. The compound of Formula (1) of the present invention may be converted to their salts according to any of the conventional methods, and the salt formation could be easily carried out by a person skilled in the art based on the structure of Formula (1) without additional explanations thereon.

On the other hand, the compound of Formula (1) of the present invention may have an asymmetric carbon center(s) in the structure, and so may exist in the form of an R or S isomer, a racemate, a mixture of diastereomers, or an individual diastereomer. All such isomers are also included in the scope of the present invention.

The present invention also provides processes for preparing the compound of Formula (1). Hereinafter, the processes for preparing the compound of Formula (1) are illustrated by exemplary reaction schemes for the purpose of better understanding. However, a skilled artisan in the field to which the present invention pertains could prepare the compound of Formula (1) via various routes according to their structures, and such processes should be construed to fall under the scope of the present invention. In other words, the compound of Formula (1) may be prepared by optionally combining various synthetic methods which are described in the present specification or disclosed in the prior arts. The processes for preparing the compound of Formula (1) cover even such processes, and are not limited to those explained below.

First of all, the compound of Formula (1) may be prepared according to the following Reaction Scheme 1 by reducing the nitro group of the compound (2) to prepare the amine compound (3), and by carrying out reductive amination on the formed amine group with compound (4).

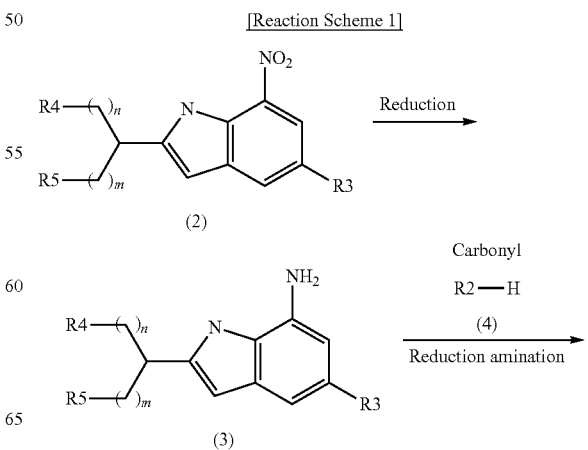

[Reaction Scheme 1]

-continued

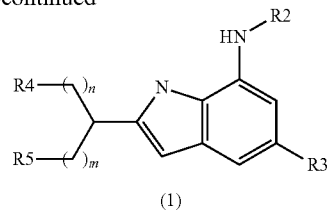

(1)

In the above Reaction Scheme 1, n, m, R2, R3, R4 and R5 are the same as defined above.

Compound (3) may be prepared by reducing compound (2). The reduction may be carried out by the use of an acid catalyst and a metal, or a metallic catalyst in the presence of hydrogen gas.

An acid used in the reduction using an acid catalyst and a metal is, for example, inorganic acid such as hydrochloric acid, sulfuric acid, nitric acid, phosphoric acid, etc.; organic carboxylic acid such as acetic acid, trifluoroacetic acid, etc.; or salt of amine acid such as ammonium chloride, etc., and preferably hydrochloric acid, acetic acid or ammonium chloride. An acid is conventionally used in an amount of 0.01-10 equivalents based on 1 equivalent of compound (2), and preferably 0.1-5 equivalents. A metal used in the reduction is, for example, iron, zinc, lithium, sodium, or tin (usually, tin chloride), and preferably iron, zinc or tin chloride. A metal is conventionally used in an amount of 1-20 equivalents based on 1 equivalent of compound (2), and preferably 1-10 equivalents. The reaction using a metal in the presence of an acid catalyst may be carried out in an inert solvent. An inert solvent is—for example, alkyl alcohol such as methanol, ethanol, etc.; ether such as tetrahydrofuran, diethyl ether, etc., or alkyl ester such as ethyl acetate, etc., and preferably methanol, ethanol, tetrahydrofuran or ethyl acetate. The reaction temperature is conventionally −10-200° C., and preferably 25-120° C. The reaction time is conventionally 10 minutes-60 hours, and preferably 10 minutes-12 hours.

A metallic catalyst used in the reaction using a metallic catalyst in the presence of hydrogen gas is, for example, palladium, nickel, platinum, ruthenium, rhodium, etc., and preferably palladium or nickel. A metallic catalyst is conventionally used in an amount of 0.001-2 equivalents based on 1 equivalent of compound (2), and preferably 0.01-1 equivalent. The pressure of hydrogen gas is conventionally 1-10 atm, and preferably 1-3 atm. This reaction may be carried out in an inert solvent—for example, alkyl alcohol such as methanol, ethanol, etc.; ether such as tetrahydrofuran, diethyl ether, etc.; or alkyl acetate such as methyl acetate, ethyl acetate, etc., and preferably methanol, ethanol or ethyl acetate. The temperature of the reaction using a metallic catalyst is conventionally −10-200° C., and preferably 25-50° C. The reaction time is conventionally 10 minutes-60 hours, and preferably 10 minutes-12 hours.

Compound (1) may be prepared via reductive amination on the amine group of compound (3).

Reductive amination may be carried out via the reaction with aldehyde or ketone using a reducing agent, and an acid catalyst may be used if necessary. The amount of aldehyde or ketone is conventionally 1-10 equivalents based on 1 equivalent of compound (3), and preferably 1-3 equivalents. A reducing agent used in the reaction may be sodium borohydride, sodium cyanoborohydride (NaBH$_3$CN), sodium triacetoxyborohydride (NaBH[OAc]$_3$), etc. A reducing agent is conventionally used in an amount of 1-10 equivalents based on 1 equivalent of compound (3), and preferably 1-3 equivalents. An acid catalyst used in the reaction is, for example, inorganic acid such as hydrochloric acid, sulfuric acid, nitric acid, phosphoric acid, etc.; organic carboxylic acid such as acetic acid, trifluoroacetic acid, etc.; or salt of amine acid such as ammonium chloride, etc., and preferably hydrochloric acid or acetic acid. An acid is conventionally used in an amount of 0.1-10 equivalents based on 1 equivalent of compound (3), and preferably 1-5 equivalents. This reaction may be carried out in an inert solvent—for example, ether such as tetrahydrofuran, diethyl ether, etc.; or chloroalkane such as dichloromethane, chloroform, dichloroethane, etc., and preferably dichloroethane or chloroform. The temperature of the reaction is conventionally −10-100° C., and preferably −10-50° C. The reaction time is conventionally 10 minutes-60 hours, and preferably 10 minutes-12 hours.

Compound (2) may be prepared by coupling of acetylene compound (5) with compound (6) to obtain compound (7) and cyclizing the obtained compound (7) as the following Reaction Scheme 2.

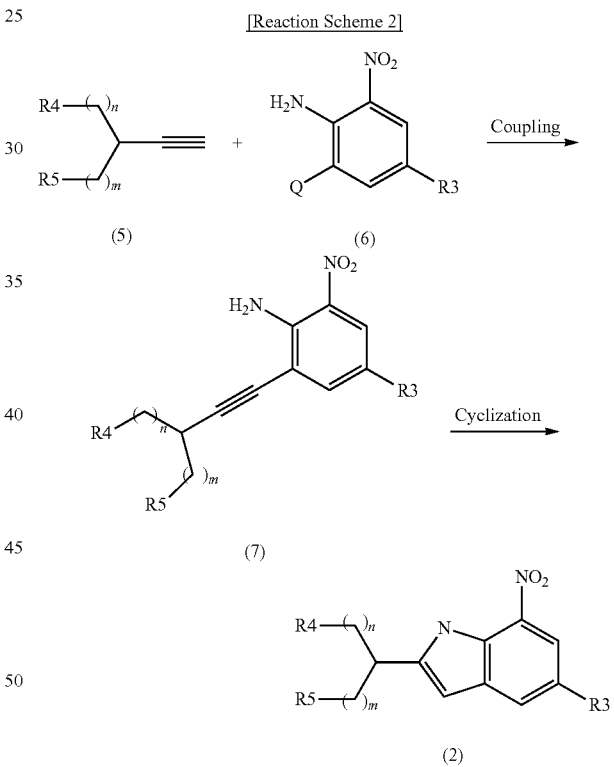

[Reaction Scheme 2]

In the above Reaction Scheme 2, n, m, R3, R4 and R5 are the same as defined above, and Q represents iodo or bromo.

The preparation of acetylene compound (7) may be carried out by adding a base in the presence of a metallic catalyst, where Pd(II), Cu(I), etc. are used as the metallic catalyst, and Et$_3$N, Et$_2$N(iPr), DBU, N-methyl-morpholine, methyl-pyrrolidine, K$_2$CO$_3$, etc. are used as the base.

Acetylene compound (5) is commercially available or may be synthesized from aldehyde according to the following Reaction Scheme 3.

[Reaction Scheme 3]

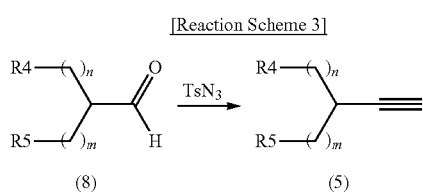

In the above Reaction Scheme 3, n, m, R4 and R5 are the same as defined above.

Compound (6) may be synthesized from commercially available aniline compound (9) according to the following Reaction Scheme 4.

[Reaction Scheme 4]

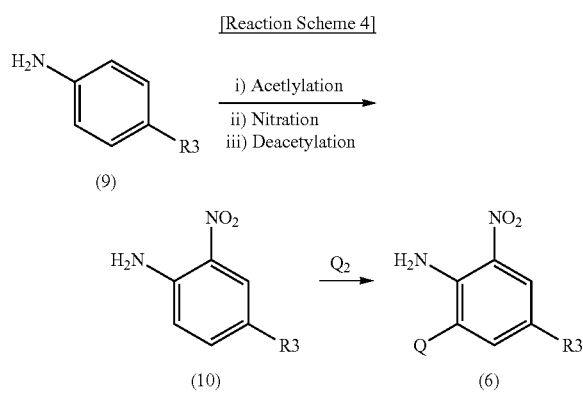

In the above Reaction Scheme 4,

R3 is the same as defined above, and

Q represents iodo or bromo.

The halogenating material for preparing compound (6) may be selected from iodine, bromine, iodomonobromide and iodomonochloride, which may be used along with a silver ion such as silver nitrate ($AgNO_3$), silver carbonate ($AgCO_3$), silver sulfate ($Ag_2SO_4$), etc.

Conventional acetylation and nitration reactions are used for obtaining compound (10) from compound (9). The nitration reaction may be carried out by using undiluted nitric acid at a low temperature (−15 to 0° C.), or in various solvents such as dichloroethane or dichloromethane may be used together.

The compound in which R4 and R5 together form a ring may be synthesized according to the following Reaction Scheme 5.

[Reaction Scheme 5]

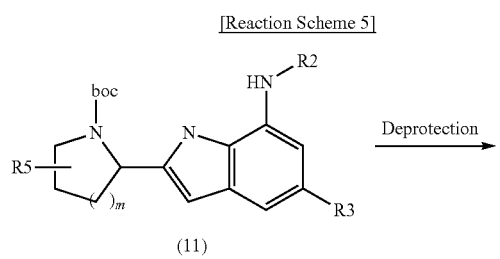

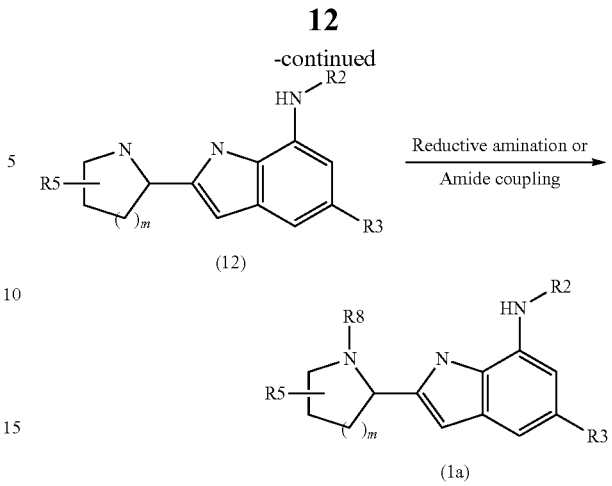

In the above Reaction Scheme 5, m, R2, R3, R5 and R8 are the same as defined above.

Compound (11) may be synthesized according to Reaction Scheme 2, and reductive amination may be carried out in the same manner as in Reaction Scheme 1.

Examples of known coupling agents used in amide coupling include, but are not limited to, a mixture of carboimide such as dicyclohexylcarbodiimide (DCC), 1-(3-dimethylaminopropyl)-3-ethylcarbodiimide (EDC), 1,1'-dicarbonyldiimidazole (CDI), etc. with 1-hydroxy-benzotriazole (HOBT) or 1-hydroxy-7-azabenzotriazole (HOAT), or bis-(2-oxo-3-oxazolidinyl)-phosphinic acid chloride (BOP-Cl), diphenylphosphoryl azide (DPPA), N-[dimethylamino-1H-1,2,3-triazole [4,5-b] pyridin-1-yl-methylene]-N-methyl methane aminium (HATU), etc. A coupling agent is conventionally used in an amount of 1-10 equivalents based on 1 equivalent of compound (12), and preferably 1-3 equivalents. HOBT or HOAT is conventionally used in an amount of 1-10 equivalents based on 1 equivalent of compound (12), and preferably 1-3 equivalents. When hydrochloric acid salt of amine is used in coupling reaction, an acid should be removed by the use of a base. The base used at this time is an organic base such as triethylamine or diisopropylethylamine. The base is conventionally used in an amount of 1-10 equivalents based on 1 equivalent of compound (12), and preferably 1-3 equivalents. The coupling reaction may be carried out in an inert solvent such as tetrahydrofuran, diethylether or N,N-dimethylformamide. The temperature of the reaction is conventionally −10-200° C., and preferably 25-120° C. The reaction time is conventionally 10 minutes-60 hours, and preferably 10 minutes-12 hours.

The compounds whose preparation methods are not specifically explained in the present specification are known per se, or those that can be prepared from a known compound according to a known process or a similar process thereto.

In the processes according to the present invention, mixtures are conventionally separated by column chromatography. In the case of a final product, it can be separated after completion of reaction by recrystallization or normal or reverse-phased HPLC (Waters, Delta Pack, 300×50 mm I.D., C18 5 μm, 100 A). When the product is purified by recrystallization or HPLC, the compound may be obtained in the form of a salt with trifluoroacetic acid. When a hydrochloric acid salt is desirable, ion exchange resin can be used.

As explained above, the compounds according to the present invention, starting materials, intermediates, etc. for the preparation thereof may be obtained by various processes, and such processes for preparing the compound of Formula (1) should be construed to fall under the scope of the present invention.

The present invention further provides a composition for the prevention or treatment of necrosis and associated diseases, which comprises a therapeutically effective amount of the compound of Formula (1), a pharmaceutically acceptable salt or isomer thereof as an active ingredient together with a pharmaceutically acceptable carrier or diluent.

In addition, the present invention provides a method for the prevention or treatment of necrosis and associated diseases using the above composition.

Necrosis and associated diseases which can be treated and/or prevented according to the present invention include acute/chronic hepatic disease (e.g., hepatitis, hepatic fibrosis, hepatocirrhosis), neurodegenerative disease (e.g., dementia, Parkinson's disease, Huntington's disease), ischemic cardiac disease, reperfusion injury, ischemic stroke or ischemic injury, pancreatitis, bacterial/viral sepsis, diabetes mellitus or diabetic complications, diabetic vascular disease (in particular, these diabetes are caused by pancreatic cell destroying substances, and mediated by virus, hyperglycemia, fatty acid, diet, toxin, streptozotocin and the like), necrotizing procolitis, cystic fibrosis, rheumatoid arthritis, degenerative arthritis, nephropathy, bacterial infection, viral infection (e.g., HIV), multiple sclerosis, leukemia, lymphoma, neonatal respiratory distress syndrome, asphyxia, tuberculosis, endometriosis, angiasthenia, psoriasis, chilblain, steroid treatment complications, gangrene, pressure sores, hemoglobinuria, burns, hyperthermia, Crohn's disease, celiac disease, compartment syndrome, spinal cord injury, glomerulonephritis, muscular dystrophy, metabolic inherited disease, mycoplasmal disease, anthrax, Andersen's disease, congenital mitochondrial disease, phenylketonuria, placental infarction, syphilis, aseptic necrosis etc. In addition, necrosis and associated diseases caused by drugs and toxic substances are selected from the group consisting of the necrosis associated with alcoholism, the exposure to, and/or administration and/or self-administration of cocaine, drugs (e.g., paracetamol), antibiotics, anti-cancer agent, adriamycin, puromycin, bleomycin, NSAID, cyclosporine, chemical toxins (e.g., carbon tetrachloride, cyanide, methanol, ethylene glycol), poison gas, agrochemicals, heavy metals (e.g., lead, mercury, cadmium), or injury due to the exposure to radioactivity/UV and associated necrosis thereof.

Specifically, the composition according to the present invention exhibits not only the effects for hepatoprotection and hepatic functional improvement, but also shows the prophylactic and therapeutic effects on chronic hepatic diseases such as fatty liver, hepatic fibrosis, hepatocirrhosis, etc. and acute/chronic hepatic disease such as hepatitis, etc. caused by virus or drugs. Consequently, complications of hepatic disease including, but not limited to, portal hypertension also may be prevented or treated. More particularly, the medical composition according to the present invention is also effective for the treatment or prevention of hepatic diseases selected from liver transplantation, alcoholic or non-alcoholic fatty liver, hepatic fibrosis, hepatocirrhosis and hepatitis caused by virus or drugs, and is effective for alcoholic acute/chronic hepatic disease.

Furthermore, the composition according to the present invention is effective for the treatment or prevention of fatty acid-induced fatty liver or acute/chronic hepatic disease derived from fatty liver.

As used herein, "treatment" means the interruption or delay of the progress of the disease when applied to a subject showing the onset of disease symptoms, and "prevention" means the interruption or delay of the sign of the onset of disease when applied to a subject who does not show, but is at risk of, the onset of disease symptoms.

The above-mentioned "pharmaceutical composition" may comprise pharmaceutically acceptable carriers, diluents, excipients, or their combinations, if needed, together with the compounds of the present invention. A pharmaceutical composition facilitates the administration of the compound into a living organism. There exist a number of techniques to administer the compound, and they include, but are not limited to, oral, injectable, aerosol, parenteral and topical administration.

As used herein, "carrier" means a substance which facilitates the incorporation of the compound into the cells or tissues. For example, dimethyl sulfoxide (DMSO) is a typical carrier which is used to facilitate the introduction of various organic compounds into the cells or tissues of living organisms.

As used herein, "diluent" is defined as a substance that is diluted in water which dissolves the compound, as well as stabilizes the biologically active form of the subject compound. The salts dissolved in buffer solution are utilized as diluents in the art. A typically used buffer solution is phosphate-buffered saline which mimics the salt form of human solution. Buffer diluents rarely alter the biological activities of the compound, as the buffer salts can control the pH of solution at low concentration.

As used herein, "pharmaceutically acceptable" means the property that does not impair the biological activities and physical properties of the compound.

The compound of the present invention can be formulated as various pharmaceutical dosage forms according to the desired purpose. For the preparation of the pharmaceutical composition of the present invention, active ingredient, specifically, the compound of Formula (1), a pharmaceutically acceptable salt or isomer thereof is mixed together with various pharmaceutically acceptable carriers which can be selected according to the formulation to be prepared. For example, the pharmaceutical composition of the present invention can be formulated as injectable preparation, oral preparation, etc., according to the desired purpose.

The compound of the present invention can be formulated by the methods known in the art, which utilize pharmaceutical carriers and excipients known in the art, and can be incorporated into containers of unit dose form or multi-dose form. The form of the preparation can be solutions, suspensions or emulsions in oily or aqueous media, and contain typical dispersing agents, suspending agents or stabilizers. Furthermore, for example, it can be a form of dry powder which is intended to be reconstructed by dissolving in sterile, pyrogen-free water prior to use. The compound of the present invention also can be formulated into suppository forms utilizing typical suppository base such as cocoa butter or other glycerides. As solid dosage forms for oral administration, capsules, tablets, pills, powder and granules can be prepared, and capsules and tablets are especially useful. Preferably, tablets and pills are prepared as enteric coated forms. Solid dosage forms can be prepared by mixing the compounds of the present invention together with carriers such as one or more inert diluents such as sucrose, lactose, starch, etc., lubricants such as magnesium stearate, disintegrants, binders, etc.

If needed, the compound of the present invention or the pharmaceutical composition containing the same can also be administered in combination with other active agents including cytoprotective agents with various action mechanisms of different types, especially the existing agents utilized for hepatoprotection, hepatic functional improvement, and prevention or treatment of hepatic disease—hepatocyte regeneration promoters, hepatic functional adjuvants, anti-viral agents, immunosuppressants, fibrosis inhibitors, etc.

The compound of the present invention or the pharmaceutical composition containing the same can be co-administered with a prophylactic or therapeutic agent for any drug-induced necrosis and associated diseases. These drugs include those for any disease group, such as antibiotics, anti-cancer agents, anti-viral agents, anti-infectives, anti-inflammatory agents, anti-coagulants, lipid-improving agents, cell death inhibitors, anti-hypertensive agents, anti-diabetic/anti-obesity agents, therapeutic agents for cardiovascular disease, therapeutic agents for neurodegenerative disease, anti-aging agents, therapeutic agents for metabolic disease, etc.

The compound of the present invention or the pharmaceutical composition containing the same can be used for the prevention of cell injury and subsequent necrosis and associated diseases derived by various causes such as toxins, and these causes include reactive oxygen species (ROS), heavy metals, alcohol, food, supplements, radiation, diet, etc.

The dosage of the compound of Formula (1) depends on the prescription of a physician, taking into account such factors as body weight, sex, age, condition of health, and diet of the patient, specific nature of the disease, administration time of the agent, administration method, mixing ratio of agents, and severity of the disease, etc. However, dosage needed for the treatment of an adult is typically from about 1.0 mg to 2,000 mg per day, depending on the intensity and frequency of the administration. When administered to an adult via intramuscular or intravenous routes, total dosage typically from about 1.0 mg to 300 mg per day will be sufficient when separately administered in a single dosage, but for some patients a higher daily dosage may be desirable.

The present invention further provides a method of preparing the composition for the prevention or treatment of necrosis and associated diseases, which comprises the step of mixing the compound of Formula (1), a pharmaceutically acceptable salt or isomer thereof as an active ingredient together with a pharmaceutically acceptable carrier or diluent.

The pharmaceutical composition according to the present invention can show hepatoprotection and hepatic functional improvement, and can prevent or treat acute/chronic hepatic diseases and complications of hepatic disease such as portal hypertension, but is not limited thereto.

ADVANTAGEOUS EFFECTS OF THE INVENTION

A novel compound according to the present invention not only exhibits the effects for hepatoprotection and hepatic functional improvement, but also can be used in the prevention or treatment of chronic hepatic diseases such as fatty liver, hepatic fibrosis, hepatocirrhosis, etc. and acute/chronic hepatic diseases such as hepatitis, etc. caused by virus or drugs. In addition, the compound of the present invention shows necrosis inhibitory efficacy in cells from the pancreas, kidney, brain, cartilage, and heart.

Therefore, the compound of the present invention can be useful in the prevention and treatment of necrosis and associated diseases.

MODE FOR THE INVENTION

Hereinafter, the present invention is explained in more detail with the following examples. However, it must be understood that the protection scope of the present invention is not limited to the examples. In the following Preparation Examples and Examples, M means molar concentration, and N means normal concentration.

The abbreviations used in the following Preparation Examples and Examples are as follows:
Ac: acetyl
BOC: t-butoxycarbonyl
Bu: butyl
c-Pen: cyclopentyl
c-Hex: cyclohexyl
DCM: dichloromethane
DIPEA: diisopropylethylamine
DMAP: 4-dimethylaminopyridine
DMF: N,N-dimethylformamide
EDC: 1-(3-dimethylaminopropyl)-3-ethylcarbodiimide, hydrochloride
Et: ethyl
Hex: n-hexane
HOBT: hydroxybenzotriazole
HBTU: 2-(1H-benzotriazol-1-yl)-1,1,3,3-tetramethyluronium hexafluorophosphate
i-Pr: isopropyl
i-Pen: isopentyl
Me: methyl
Ph: phenyl
TEA: triethylamine
TFA: trifluoroacetic acid
THF: tetrahydrofuran
THP: tetrahydropyran
TMS: trimethylsilyl Preparation Example 1

2-Iodo-4-methyl-6-nitro-phenylamine

Commercially available 4-methyl-2-nitro-phenylamine (20 g, 131.5 mmol) was dissolved in ethanol (300 ml), to which were added silver nitrate (27 g, 157.7 mmol) and iodine (40 g, 157.7 mmol), and the mixture was stirred at room temperature for 8 hours. After completion of the reaction, the mixture was filtered through Cellite, washed with ethyl acetate (100 ml), and concentrated. The reactant was added with water, extracted with ethyl acetate, washed with saturated sodium chloride solution, and dried with anhydrous magnesium sulfate to give the title compound (29 g, Yield 69%).

$^1$H-NMR (500 MHz, CDCl$_3$); δ 7.94 (s, 1H), 7.75 (s, 1H), 6.48 (br s, 2H), 2.23 (s, 3H)

Preparation Example 2

2-Iodo-4-chloro-6-nitro-phenylamine

Commercially available 4-chloro-2-nitro-phenylamine and iodine were reacted in the same manner as in Preparation Example 1 to give the title compound.
Mass [M+1]=298 (M+H)

Preparation Example 3

4-Amino-3-iodo-5-nitro-benzoic acid ethyl ester

Step A: 4-Amino-3-nitro-benzoic acid ethyl ester

Commercially available 4-amino-3-nitro-benzoic acid (90 g, 50 mmol) was added to sulfuric acid ethanol solution (sulfuric acid:ethanol=9:1, 100 ml) and heated at 80° C. for 12 hours. After completion of the reaction, the reactant was neutralized by using NaOH (6N) solution, extracted with ethyl acetate, and the organic material was dried with anhydrous magnesium sulfate. The solvent was removed under reduced pressure, and the reactant was recrystallized with normal hexane and ethyl acetate to give the title compound (96 g, 92%).

Step B: 4-Amino-3-iodo-5-nitro-benzoic acid ethyl ester

4-Amino-3-nitro-benzoic acid ethyl ester obtained in Step A and iodine were reacted in the same manner as in Preparation Example 1 to give the title compound.
MS[M+1]=210(M+1)

Preparation Example 4

((R)-1-Benzyl-2-prop-2-ynyl)-carbamic acid t-butyl ester

Step A: ((R)-1-Benzyl-2-oxo-ethyl)-carbamic acid t-butyl ester

Commercially available ((R)-1-benzyl-2-hydroxy-ethyl)-carbamic acid t-butyl ester (3 g, 11.9 mmol) was dissolved in dichloromethane (60 ml) and methyl sulfoxide (20 ml), to which were added triethylamine (4.7 g, 29.5 mmol) and sulfur trioxide pyridine (4.8 g, 157.7 mmol), and the mixture was stirred at room temperature for 2 hours. After completion of the reaction, the reactant was added with water, extracted with ethyl acetate, the resulting organic material was washed with saturated sodium chloride solution, dried with anhydrous magnesium sulfate and filtered, and the solvent was removed under reduced pressure. The residue was purified by column chromatography to give the title compound (2.7 g, 91%).
MS[M+1]=250(M+1)

Step B: ((R)-1-Benzyl-2-prop-2-ynyl)-carbamic acid t-butyl ester

Tosyl chloride (10 g, 52.4 mmol) was dissolved in acetone (100 ml) and water (100 ml), to which was added sodium azide (3.4 g, 52.4 mmol), and the mixture was stirred at room temperature for 2 hours. After completion of the reaction, the acetone was removed under reduced pressure, and water was added thereto. The reactant was extracted with diethyl ether, and the resulting organic material was washed with saturated sodium chloride solution, dried with anhydrous magnesium sulfate and filtered. The solvent was removed under reduced pressure to give tosyl azide (9.8 g, 88%).
The obtained tosyl azide (2.48 g, 12.6 mmol) was dissolved in acetonitrile (50 ml), to which were added commercially available dimethyl acetophosphonate (1.94 g, 11.7 mmol) and potassium carbonate (3.23 g, 23.9 mmol), and the mixture was stirred at room temperature for 3 hours. ((R)-1-benzyl-2-oxo-ethyl)-carbamic acid t-butyl ester (2.66 g, 10.6 mmol) obtained in Step A dissolved in methanol (50 ml) was slowly added thereto. Potassium carbonate (2.94 g, 21.3 mmol) was added thereto, and the mixture was stirred for 18 hours. After completion of the reaction, the reactant was filtered through Cellite and washed with acetonitrile (100 ml). The solvent was removed under reduced pressure. The reactant was diluted with diethylether (100 ml), to which was added water (100 ml), and extracted with diethyl ether. The resulting organic material was dried with anhydrous magnesium sulfate. The solvent was removed under reduced pressure, and the residue was purified by column chromatography to give the title compound (1.65 g, 63%).
MS[M+1]=246(M+1)

Preparation Example 5

(S)-2-ethynyl-pyrrolidin-1-carboxylic acid t-butyl ester

Commercially available N—BOC-proline aldehyde was reacted in the same manner as in Preparation Example 4 to give the title compound.
MS[M+1]=196(M+1)

Preparation Example 6

(2S, 4R)-4-benzyloxy-2-ethynyl-pyrrolidin-1-carboxylic acid t-butyl ester

Commercially available (2S, 4R)-4-benzyloxy-2-formyl-pyrrolidin-1-carboxylic acid t-butyl ester was reacted in the same manner as in Preparation Example 4 to give the title compound.
MS[M+1]=302(M+1)

Preparation Example 7

4-Ethynyl-piperidin-1-carboxylic acid t-butyl ester

Commercially available 4-formyl-piperidin-1-carboxylic acid t-butyl ester was reacted in the same manner as in Preparation Example 4 to give the title compound. MS[M+1]=210(M+1)

Preparation Example 8

((S)-1-benzyl-2-prop-2-ynyl)-carbamic acid t-butyl ester

Commercially available (1-formyl-2-phenyl-ethyl)-carbamic acid t-butyl ester was reacted in the same manner as in Preparation Example 4 to give the title compound.
MS[M+1]=246(M+1)

Preparation Example 9

(R)-4-ethynyl-2,2-dimethyl-oxazolidin-3-carboxylic acid t-butyl ester

Step A: (S)-2,2-dimethyl-oxazolidin-3,4-dicarboxylic acid 3-t-butyl ester 4-methyl ester 2-t-Butoxycarbonylamino-3-hydroxy-propionic acid methyl ester (11.4 g, 52 mmol) was dissolved in dichloromethane (100 ml) and 2,2-dimethoxypropane (200 ml), to which was added toluene-4-sulfonic acid (0.1 g, 0.6 mmol), and stirred for 3 hours. After completion of the reaction, triethylamine (1 ml) was added thereto, the solvent was removed under reduced pressure, and the residue was purified by column chromatography to give the title compound (11.4 g, 92%).

Step B: (R)-4-hydroxymethyl-2,2-dimethyl-oxazolidin-3-carboxylic acid 3-t-butyl ester (R)-2,2-dimethyl-oxazolidin-3,4-dicarboxylic acid 3-t-butyl ester 4-methyl ester (11.4 g, 44.0 mmol) obtained in Step A was dissolved in dichloromethane (100 ml), to which was added diisopropyl aluminum hydride (1.5M toluene, 66 ml) at −78° C. While heating to room temperature, the mixture was stirred for 18 hours. After completion of the reaction, methanol (20 ml) and sodium hydroxide solution (1 N, 200 ml) were slowly added thereto, and the organic material was extracted with dichloromethane and dried with anhydrous magnesium sulfate. The solvent was removed under reduced pressure, and the residue was purified by column chromatography to give the title compound (9.7 g, 95%).

Step C: (R)-4-ethynyl-2,2-dimethyl-oxazolidin-3-carboxylic acid t-butyl ester (R)-4-hydroxymethyl-2,2-dimethyl-oxazolidin-3-carboxylic acid 3-t-butyl ester obtained in Step B was reacted in the same manner as in Preparation Example 4 to give the title compound.
MS[M+1]=226(M+1)

Preparation Example 10

[(R)-1-(5-chloro-7-nitro-1H-indol-2-yl)-2-phenyl-ethyl]-carbamic acid t-butyl ester

Step A: [(R)-3-(2-amino-5-chloro-3-nitro-phenyl)-1-benzyl-prop-2-ynyl]-carbamic acid t-butyl ester (R)-4-ethynyl-2,2-dimethyl-oxazolidin-3-carboxylic acid t-butyl ester (1.65 g, 6.7 mmol) obtained in Preparation Example 9 and 2-iodo-4-chloro-6-nitro-phenylamine (2.0 g, 6.7 mmol) obtained in Preparation Example 2 were dissolved in tetrahydrofuran (30 ml), and then triethylamine (2.04 g, 20.2 mmol), dichloro(bistriphenylphosphine)palladium (II) (236 mg, 0.33 mmol), and copper (I) iodide (64 mg, 0.33 mmol) were added thereto. The mixture was stirred at room temperature for 8 hours. After completion of the reaction, the reactant was diluted with water, and extracted with ethyl acetate. The resulting organic material was washed with saturated sodium chloride solution, dried with anhydrous magnesium sulfate, and filtered. The solvent was removed under reduced pressure, and the residue was purified by column chromatography to give the title compound (1.75 g, 63%).
MS[M+1]=416(M+1)

Step B: [(R)-1-(5-chloro-7-nitro-1H-indol-2-yl)-2-phenyl-ethyl]-carbamic acid t-butyl ester

[(R)-3-(2-amino-5-chloro-3-nitro-phenyl)-1-benzyl-prop-2-ynyl]-carbamic acid t-butyl ester (1.75 g, 4.21 mmol) obtained in Step A was dissolved in N-methyl-pyrrolidinone (15 ml), to which was added potassium t-butoxide (944 mg, 8.41 mmol), and then stirred at room temperature for 3 hours. After completion of the reaction, the reactant was diluted with water, and the organic material was extracted with ethyl acetate. The resulting organic material was washed with saturated sodium chloride solution, dried with anhydrous magnesium sulfate, and filtered. The solvent was removed under reduced pressure, and the residue was purified by column chromatography to give the title compound (674 mg, 39%).
MS[M+1]=416(M+1)

Preparation Examples 11 to 23

Commercially available acetylene compound or acetylene compounds obtained in Preparation Examples 4 to 9, and iodine compounds obtained in Preparation Examples 1 and 2 were reacted in the same manner as in Preparation Example 10 to give the compounds listed in the following table.

| Preparation Example | R' | R3 | Mass [M + 1] |
|---|---|---|---|
| 11 | (S)-1-BOC-pyrrolidin-2-yl | Cl | 366 |
| 12 | (3R,2S)-1-BOC-3-benzyloxy-pyrrolidin-2-yl | Cl | 472 |
| 13 | 1-BOC-piperidin-4-yl | Me | 360 |
| 14 | 1-BOC-piperidin-4-yl | Cl | 380 |
| 15 | 1-BOC-piperidin-4-yl | C(O)OEt | 418 |
| 16 | (R)-1-BOC-amino-2-phenyl ethyl-1-yl | Me | 396 |
| 17 | (S)-1-BOC-amino-2-phenyl ethyl-1-yl | Cl | 416 |
| 18 | (S)-1-BOC-amino-2-phenyl ethyl-1-yl | Me | 396 |
| 19 | THPO—CH$_2$— | Me | 291 |
| 20 | THPO—CH$_2$— | Cl | 311 |
| 21 | THPO—CH$_2$—CH$_2$— | Cl | 324 |
| 22 | Cyclohexyl | Me | 259 |
| 23 | (S)-N-BOC-2,2-dimethyl-oxazolidin-4-yl | Cl | 396 |

Example 1

4-(5-Chloro-7-cyclopentylamino-1H-indol-2-ylmethyl)-piperazin-2-one

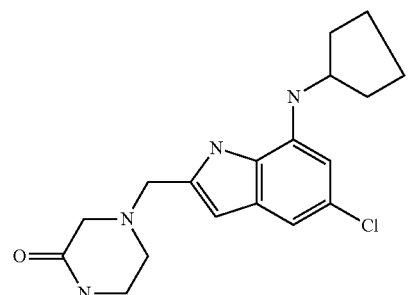

4-(5-Chloro-7-cyclopentylamino-1H-indol-2-ylmethyl)-piperazin-2-one

Step A: (5-Chloro-7-nitro-1H-indol-2-yl)-methanol

5-Chloro-7-nitro-2-(tetrahydro-pyran-2-yloxymethyl)-1H-indole (1.95 g, 6.3 mmol) obtained in Preparation Example 20 was dissolved in methanol (200 ml), to which was added toluene-4-sulfonic acid (0.1 g, 0.6 mmol), and stirred at room temperature for 2 hours. After completion of the reaction, sodium bicarbonate (100 mg, 1.2 mmol) was added thereto, the solvent was removed under reduced pressure, and the reactant was recrystallized by the use of water and methanol to give the title compound (1.20 g, 5.30 mmol).

MS[M+1]=227(M+1)

Step B: 5-Chloro-2-iodomethyl-7-nitro-1H-indole (5-Chloro-7-nitro-1H-indol-2-yl)-methanol (155 mg, 0.68 mmol) obtained in Step A was dissolved in THF (10 ml), to which were added imidazole (140 mg, 2.0 mmol) and triphenylphosphine (269 g, 1.03 mmol), iodine (261 mg, 1.03 mmol) was added thereto, and the mixture was stirred for 10 minutes. After completion of the reaction, the solvent was removed under reduced pressure, and the residue was purified by column chromatography to give the title compound (130 mg, 66%).

MS[M+1]=337(M+1)

Step C: 4-(5-Chloro-7-nitro-1H-indol-2-ylmethyl)-piperazin-2-one

5-Chloro-2-iodomethyl-7-nitro-1H-indole (130 mg, 0.37 mmol) obtained in Step B was dissolved in acetonitrile (10 ml), to which was added piperazin-2-one (111 mg, 1.01 mmol), and stirred at 80° C. for 18 hours. After completion of the reaction, the solvent was removed under reduced pressure, and water (20 ml) was added thereto. The organic material was extracted with ethyl acetate, and dried with anhydrous magnesium sulfate. The solvent was removed under reduced pressure, and the residue was purified by column chromatography to give the title compound (89 mg, 78%).

MS[M+1]=309(M+1)

Step D: 4-(7-Amino-5-chloro-1H-indol-2-ylmethyl)-piperazin-2-one 4-(5-Chloro-7-nitro-1H-indol-2-ylmethyl)-piperazin-2-one (90 mg, 0.29 mmol) obtained in Step C was dissolved in tetrahydrofuran (3 ml), methanol (3 ml) and water (3 ml), to which were added ammonium chloride (156 mg, 2.92 mmol) and iron powder (82 mg, 1.47 mmol), and stirred at 70° C. for 1 hour. After completion of the reaction, the reactant was filtered through Cellite and washed with tetrahydrofuran (50 ml), and the solvent was removed under reduced pressure. The reactant was diluted with ethylacetate (50 ml), water (20 ml) was added thereto, and the mixture was extracted with ethyl acetate. The resulting organic material was dried with anhydrous magnesium sulfate, the solvent was removed under reduced pressure, and the reactant was recrystallized from dichloromethane and hexane to give the title compound (69 mg, 85%).

MS[M+1]=279(M+1)

Step E: 4-(5-Chloro-7-cyclopentylamino-1H-indol-2-ylmethyl)-piperazin-2-one 4-(7-Amino-5-chloro-1H-indol-2-ylmethyl)-piperazin-2-one (27 mg, 0.10 mmol) obtained in Step D was dissolved in dichloroethane (10 ml), and acetic acid (10 mg, 0.17 mmol), cyclopentanone (0.30 mg, 0.35 mmol) and sodium triacetoxyborohydride (30 mg, 0.14 mmol) were then added dropwise thereto. The mixture was stirred at room temperature for 18 hours. After completion of the reaction, the reactant was diluted with water and extracted with dichloromethane. The resulting organic material was washed with saturated sodium chloride solution, dried with anhydrous magnesium sulfate and filtered. The solvent was removed under reduced pressure, and the residue was purified by column chromatography to give the title compound (15 mg, Yield 45%).

MS[M+11=347(M+1)

Example 2

4-{2-[5-Chloro-7-(piperidin-4-ylamino)-1H-indol-2-yl]-ethyl}-piperazin-2-one

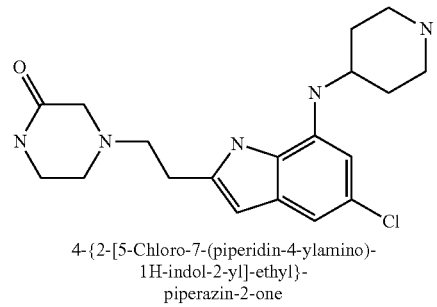 [SMILES: O=C1CN(CCc2cc3cc(Cl)cc(NC4CCNCC4)c3[nH]2)CCN1]

4-{2-[5-Chloro-7-(piperidin-4-ylamino)-1H-indol-2-yl]-ethyl}-piperazin-2-one

Step A: 4-{5-Chloro-2-[2-(3-oxo-piperazin-1-yl)-ethyl]-1H-indol-7-ylamino]-piperidin-1-carboxylic acid t-butyl ester 5-Chloro-7-nitro-2-[2-(tetrahydropyran-2-yloxy)-ethyl]-1H-indole obtained in Preparation Example 21 was reacted in the same manner as in Example 1 to give 4-{5-chloro-2-[2-(3-oxo-piperazin-1-yl)-ethyl]-1H-indol-7-ylamino]-piperidin-1-carboxylic acid t-butyl ester.

MS[M+1]=476 (M+1)

Step B: 4-{2-[5-Chloro-7-(piperidin-4-ylamino)-1H-indol-2-yl]-ethyl}-piperazin-2-one 4-{5-Chloro-2-[2-(3-oxo-piperazin-1-yl)-ethyl]-1H-indol-7-ylamino]-piperidin-1-carboxylic acid t-butyl ester (100 mg, 0.21 mmol) obtained in Step A was dissolved in dichloromethane (3 ml), trifluoroacetic acid (3 ml) was added thereto, and the mixture was stirred at room temperature for 1 hour. After completion of the reaction, the solvent was removed under reduced pressure, and the residue was purified by column chromatography to give the title compound (60 mg, Yield 60%).

MS[M+1]=376(M+1)

Example 3

4-{2-[7-(1-Acetyl-piperidin-4-ylamino)-5-chloro-1H-indol-2-yl]-ethyl}-piperazin-2-one

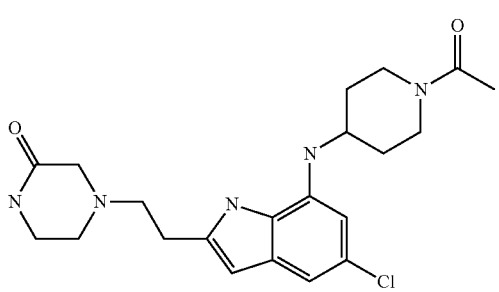

4-{2-[7-(1-Acetyl-piperidin-4-ylamino)-5-chloro-1H-indol-2-yl]-ethyl}-piperazin-2-one 4-{2-[5-Chloro-7-(piperidin-4-ylamino)-1H-indol-2-yl]-ethyl}-piperazin-2-one (30 mg, 0.079 mmol) obtained in Example 2 was dissolved in dichloromethane (5 ml), to which were added triethylamine (20 mg, 0.20 mmol) and acetic anhydride (20 mg, 0.20 mmol), and the mixture was stirred for 1 hour at room temperature. After completion of the reaction, the solvent was removed under reduced pressure, and the residue was purified by column chromatography to give the title compound (16 mg, Yield 48%).

MS[M+1]=418(M+1)

Example 4

(5-Chloro-7-cyclopentylamino-1H-indol-2-yl)-methanol

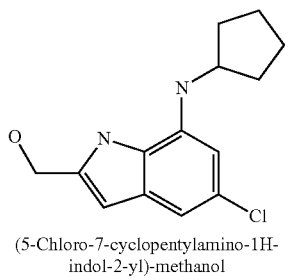 [SMILES: OCc1cc2cc(Cl)cc(NC3CCCC3)c2[nH]1]

(5-Chloro-7-cyclopentylamino-1H-indol-2-yl)-methanol

5-Chloro-7-nitro-2-(tetrahydropyran-2-yloxymethyl)-1H-indole obtained in Preparation Example 20 and cyclopentanone were reacted according to Steps D, E and A of Example 1 sequentially to give the title compound.

MS[M+1]=265(M+1)

Example 5

2-(5-Chloro-7-cyclopentylamino-1H-indol-2-yl)-ethanol

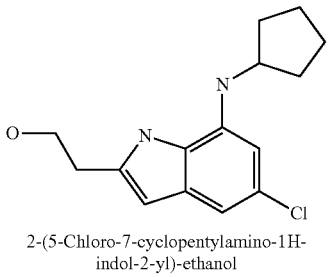 [SMILES: OCCc1cc2cc(Cl)cc(NC3CCCC3)c2[nH]1]

2-(5-Chloro-7-cyclopentylamino-1H-indol-2-yl)-ethanol

5-Chloro-7-nitro-2-(tetrahydro-pyran-2-yloxyethyl)-1H-indole obtained in Preparation Example 21 and cyclopentanone were reacted according to Steps D, E and A of Example 1 sequentially to give the title compound.

MS[M+1]=279(M+1)

Examples 6 to 25

The compounds obtained in Preparation Examples 19 to 21, commercially available amine and carbonyl compounds were reacted in the same manner as in Example 1 to give the compounds in the following table.

| Example | R2 | R3 | m | R5 | Mass |
|---|---|---|---|---|---|
| 6 | piperidin-4-yl-methyl | Me | 1 | 2-oxopiperazin-4-yl | 356 |
| 7 | tetrahydropyran-4-ylmethyl | Me | 1 | 1,1-dioxothiomorpholin-4-yl | 392 |
| 8 | cyclopentyl | Me | 1 | 1,1-dioxothiomorpholin-4-yl | 362 |
| 9 | tetrahydropyran-4-ylmethyl | Me | 1 | 2-oxopiperazin-4-yl | 343 |
| 10 | tetrahydrofuran-2-ylmethyl | Cl | 2 | 3-trifluoromethyl-5,6,7,8-tetrahydro-[1,2,4]triazolo[4,3-a]pyrazin-1-yl | 469 |
| 11 | tetrahydropyran-2-ylmethyl | Cl | 2 | 3-trifluoromethyl-5,6,7,8-tetrahydro-[1,2,4]triazolo[4,3-a]pyrazin-1-yl | 483 |
| 12 | 1-methanesulfonyl-piperidin-4-yl | Cl | 2 | 3-trifluoromethyl-5,6,7,8-tetrahydro-[1,2,4]triazolo[4,3-a]pyrazin-1-yl | 546 |
| 13 | 1-acetyl-piperidin-4-yl | Cl | 2 | 3-trifluoromethyl-5,6,7,8-tetrahydro-[1,2,4]triazolo[4,3-a]pyrazin-1-yl | 510 |
| 14 | benzyl | Cl | 2 | 2-oxopiperazin-4-yl | 383 |
| 15 | tetrahydrofuran-2-ylmethyl | Cl | 2 | 2-oxopiperazin-4-yl | 377 |
| 16 | tetrahydropyran-2-yl-methyl | Cl | 2 | 2-oxopiperazin-4-yl | 391 |
| 17 | tetrahydropyran-4-yl-methyl | Cl | 1 | 2-oxopiperazin-4-yl | 377 |
| 18 | tetrahydropyran-4-yl | Cl | 2 | 1,1-dioxothiomorpholin-4-yl | 412 |

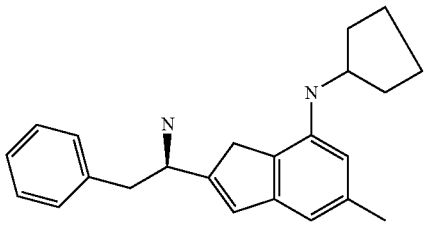

| Example | R2 | R3 | m | R5 | Mass |
|---|---|---|---|---|---|
| 19 | cyclopentyl | Cl | 2 | 1,1-dioxothiomorpholin-4-yl | 396 |
| 20 | cyclopentyl | Cl | 2 | 3-trifluoromethyl-5,6,7,8-tetrahydro-[1,2,4]triazolo[4,3-a]pyrazin-1-yl | 453 |
| 21 | tetrahydropyran-4-ylmethyl | Cl | 2 | 1,1-dioxothiomorpholin-4-yl | 426 |
| 22 | tetrahydropyran-4-ylmethyl | Cl | 2 | 2-oxopiperazin-4-yl | 391 |
| 23 | tetrahydropyran-4-ylmethyl | Cl | 2 | 3-trifluoromethyl-5,6,7,8-tetrahydro-[1,2,4]triazolo[4,3-a]pyrazin-1-yl | 482 |
| 24 | tetrahydropyran-4-ylmethyl | Cl | 2 | morpholin-4-yl | 378 |
| 25 | cyclopentyl | Me | 1 | morpholin-4-yl | 314 |

Example 26

(2-Cyclohexyl-5-methyl-1H-indol-7-yl)-cyclopentyl-amine

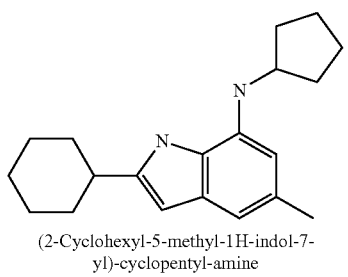 [SMILES: Cc1cc(NC2CCCC2)c2[nH]c(C3CCCCC3)cc2c1]

(2-Cyclohexyl-5-methyl-1H-indol-7-yl)-cyclopentyl-amine

2-Cyclohexyl-5-methyl-7-nitro-1H-indole obtained in Preparation Example 22 was reacted according to Steps D and E of Example 1 to give the title compound.

MS[M+1]=297(M+1)

Example 27

[2-((R)-1-amino-2-phenyl-ethyl)-5-methyl-1H-indol-7-yl]-cyclopentyl-amine

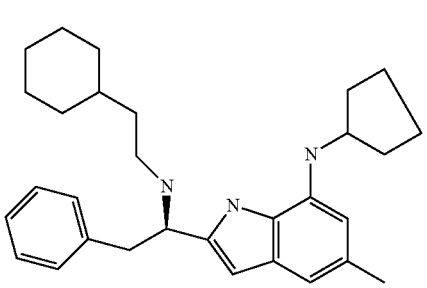

[2-((R)-1-Amino-2-phenyl-ethyl)-5-methyl-1H-indol-7-yl] cyclopentyl-amine

Step A: [(R)-1-(7-cyclopentylamino-5-methyl-1H-indol-2-yl)-2-phenyl-ethyl]-carbamic acid t-butyl ester

[(R)-1-(5-methyl-7-nitro-1H-indol-2-yl)-2-phenyl-ethyl]-carbamic acid t-butyl ester obtained in Preparation Example 16 was reacted according to Steps D and E of Example 1 sequentially to give the title compound.

MS[M+1]=434(M+1)

Step B: [2-(R)-1-amino-2-phenyl-ethyl]-5-methyl-1H-indol-7-yl]-cyclopentylamine

[(R)-1-(7-cyclopentylamino-5-methyl-1H-indol-2-yl)-2-phenyl-ethyl]-carbamic acid t-butyl ester obtained in Step A was reacted according to Step B of Example 2 to give the title compound.

MS[M+1]=334(M+1)

Example 28

{2-[(R)-1-(2-cyclohexyl-ethylamino)-2-phenyl-ethyl]-5-methyl-1H-indol-7-yl}-cyclopentylamine {2-[(R)-1-(2-Cyclohexyl-ethylamino)-2-phenyl-ethyl]-5-methyl-1H-indol-7-yl}-cyclopentyl-amine

[2-(R)-1-Amino-2-phenyl-ethyl]-5-methyl-1H-indol-7-yl]-cyclopentylamine obtained in Example 27 and cyclohexyl acetaldehyde were reacted according to Step E of Example 1 to give the title compound.

MS[M+1]=444(M+1)

Example 29

Benzyl-{5-chloro-2-[(R)-2-phenyl-1-(pyrrolidin-3-ylamino)-ethyl]-1H-indol-7-yl}-amine

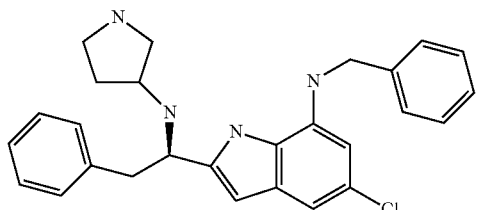

Benzyl-{5-chloro-2-[(R)-2-phenyl-1-(pyrrolidin-3-ylamino)-ethyl]-1H-indol-7-yl}-amine Step A: [2-((R)-1-amino-2-phenyl-ethyl)-5-chloro-1H-indol-7-yl]-benzyl-amine

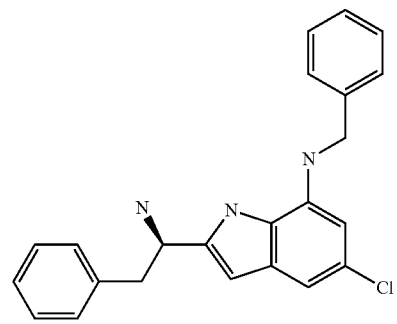

[2-((R)-1-Amino-2-phenyl-ethyl)-5-chloro-1H-indol-7-yl]-benzyl-amine

[(R)-1-(5-chloro-7-nitro-1H-indol-2-yl)-2-phenyl-ethyl]-carbamic acid t-butyl ester obtained in Preparation Example 10 and benzaldehyde were reacted according to Example 27 to give the title compound.

MS[M+1]=376(M+1)

Step B: Benzyl-{5-chloro-2-[(R)-2-phenyl-1-(pyrrolidin-3-ylamino)-ethyl]-1H-indol-7-yl}-amine The compound obtained in Step A and 3-oxo-pyrrolidin-1-carboxylic acid t-butyl ester were reacted according to Step E of Example 1 and Step C of Example 2 sequentially to give the title compound.

MS[M+1]=445(M+1)

Example 30

2-Amino-N—[(R)-1-(7-benzylamino-5-chloro-1H-indol-2-yl)-2-phenylethyl]-acetamide

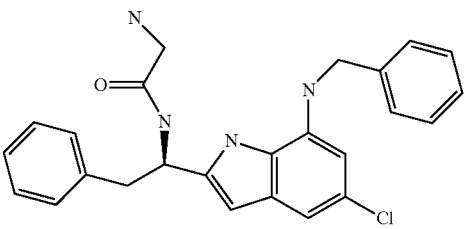

2-Amino-N-[(R)-1-(7-benzylamino-5-chloro-1H-indol-2-yl)-2-phenyl-ethyl]-acetamide Step A: {[(R)-1-(7-benzylamino-5-chloro-1H-indol-2-yl)-2-phenyl-ethyl carbamoyl]-methyl}-carbamic acid t-butyl ester The compound [2-((R)-1-amino-2-phenyl-ethyl)-5-chloro-1H-indol-7-yl]-benzyl-amine (23 mg, 0.061 mmol) obtained in Step A of Example 29 was dissolved in dichloromethane (10 ml), and triethylamine (19 mg, 0.19 mmol), EDC (18 mg, 0.094 mmol) and HOBT (17 mg, 0.13 mmol) were added thereto. After addition of BOC-glycine (16 mg, 0.091 mmol), the mixture was stirred at room temperature for 8 hours. After completion of the reaction, 1N-hydrochloric acid solution was added thereto, and the reactant was then extracted with ethylacetate. The resulting organic layer was washed with saturated sodium bicarbonate and dried with anhydrous magnesium sulfate. The reactant was filtered, the solvent was removed from the filtrate under reduced pressure, and the residue was purified by column chromatography to give the title compound (32 mg, Yield 98%).

MS[M+1]=533(M+1)

Step B: 2-Amino-N—[(R)-1-(7-benzylamino-5-chloro-1H-indol-2-yl)-2-phenylethyl]-acetamide The compound obtained in Step A was reacted according to Step B of Example 2 to give the title compound.

MS[M+1]=433(M+1)

Example 31

N—[(R)-1-(7-Benzylamino-5-chloro-1H-indol-2-yl)-2-phenyl-ethyl]-guanidine

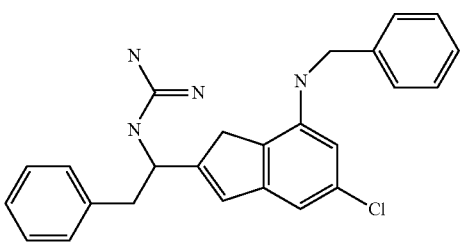

N-[(R)-1-(7-Benzylamino-5-chloro-1H-indol-2-yl)-2-phenyl-ethyl]-guanidine

Step A: N—[(R)-1-(7-Benzylamino-5-chloro-1H-indol-2-yl)-2-phenyl-ethyl]-N',N"-diBOC-guanidine The compound [2-((R)-1-amino-2-phenyl-ethyl)-5-chloro-1H-indol-7-yl]-benzyl-amine (15 mg, 0.010 mmol) obtained from Step A of Example 29 was dissolved in acetonitrile (10 ml), and triethylamine (15 mg, 0.15 mmol) and commercially available {[(E)-t-butoxycarbonylimino]-pyrazol-1-yl-methyl}-carbamic acid t-butyl ester (13 mg, 0.042 mmol) were added thereto, and the mixture was stirred at room temperature for 18 hours. After completion of the reaction, the solvent was removed under reduced pressure, and the residue was purified by column chromatography to give the title compound (17 mg, Yield 69%).
MS[M+1]=618(M+1)

Step B: N—[(R)-1-(7-benzylamino-5-chloro-1H-indol-2-yl)-2-phenyl-ethyl]-guanidine N—[(R)-1-(7-benzylamino-5-chloro-1H-indol-2-yl)-2-phenyl-ethyl]-N',N"-diBOC-guanidine obtained in Step A was reacted according to Step B of Example 2 to give the title compound.
MS[M+1]=418(M+1)

Examples 32 to 36

The methods of Examples 27 to 31 were selectively performed on the indole compounds obtained in Preparation Examples 16 to 18 and commercially available carbonyl compound to give the compounds in the following table.

| Example | R8 | * | R2 | R3 | Mass |
|---|---|---|---|---|---|
| 32 | cyclohexyl-methyl | R | cyclopentyl | Me | 430 |
| 33 | 2-amino-pyridin-3-yl-methyl | S | isopentyl | Cl | 462 |
| 34 | 3-amino-triazol-4-carbonyl | S | benzyl | Cl | 486 |
| 35 | aminomethylcarbonyl | S | isopentyl | Cl | 413 |
| 36 | guanidin-methylcarbonyl | R | benzyl | Cl | 475 |

Example 37

(S)-2-Amino-2-(5-chloro-7-cyclopentylamino-1H-indol-2-yl)-ethanol

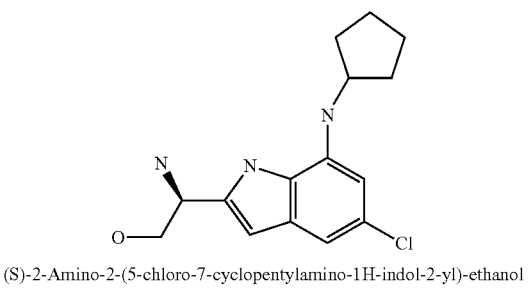 [SMILES: N[C@H](CO)c1cc2cc(Cl)cc(NC3CCCC3)c2[nH]1]

(S)-2-Amino-2-(5-chloro-7-cyclopentylamino-1H-indol-2-yl)-ethanol

Step A: [5-Chloro-2-((S)-2,2-dimethyl-oxazolidin-4-yl)-1H-indol-7-yl]-cyclopentyl-amine (S)-4-(5-Chloro-7-nitro-1H-indol-2-yl)-2,2-dimethyl-oxazolidin-3-carboxylic acid t-butyl ester obtained in Preparation Example 23 was reacted according to Example 27 to give the title compound.
MS[M+1]=334(M+1)

Step B: (S)-2-Amino-2-(5-chloro-7-cyclopentylamino-1H-indol-2-yl)-ethanol

[5-Chloro-2-((S)-2,2-dimethyl-oxazolidin-4-yl)-1H-indol-7-yl]-cyclopentyl-amine (30 g, 6.3 mmol) obtained in Step A was dissolved in methanol (10 ml), TFA (2 ml) was added thereto, and the mixture was stirred at room temperature for 2 hours. The solvent was removed under reduced pressure, and the residue was dissolved again in methanol (10 ml) and TFA (2 ml), and the mixture was stirred at room temperature for 2 hours. After completion of the reaction, the solvent was removed under reduced pressure, and the residue was purified by column chromatography to give the title compound (15 mg, Yield 57%).
MS[M+1]=294(M+1)

Example 38

((S)-5-chloro-2-pyrrolidin-2-yl-1H-indol-7-yl)-bis-(3-methyl-butyl)-amine

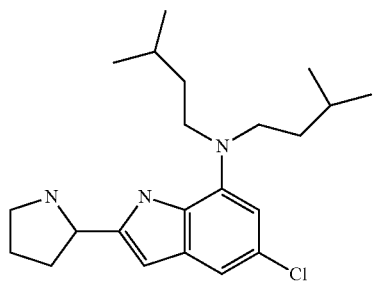

((S)-5-Chloro-2-pyrrolidin-2-yl-1H-indol-7-yl)-bis-(3-methyl-butyl)-amine (S)-1-BOC-2-(7-nitro-5-chloro-1H-indol-2-yl)-pyrrolidine obtained in Preparation Example 11 and isobutylaldehyde were reacted according to Steps D and E of Example 1 and Step B of Example 2 sequentially to give the title compound.
MS[M+1]=376(M+1)

Examples 39 to 46

The methods of Steps D and E of Example 1, Step B of Example 2, or Example 31 were selectively performed on the compounds obtained in Preparation Examples 11 and 12, and commercially available carbonyl compounds to give the compounds in the following table.

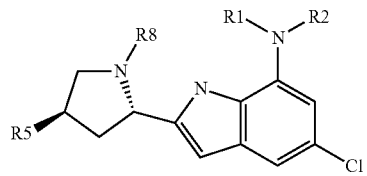

| Example | R5 | R8 | R1 | R2 | Mass |
|---|---|---|---|---|---|
| 39 | benzyl-O— | NH$_2$—C(=NH)— | H | cyclopentyl | 452 |
| 40 | H | NH$_2$—C(=NH)— | Isopentyl | isopentyl | 418 |
| 41 | H | NH$_2$—C(=NH)— | H | cyclopentyl | 346 |
| 42 | benzyl-O— | pyrrolidin-3-yl | H | cyclopentyl | 479 |
| 43 | H | pyrrolidin-3-yl | H | cyclopentyl | 373 |
| 44 | H | 2-amino-thiazol-4-ylmethyl | H | cyclopentyl | 416 |
| 45 | H | cyclopentylmethyl | Isopentyl | isopentyl | 458 |
| 46 | H | pyrrolidin-3-yl | Isopentyl | isopentyl | 445 |

Example 47

N-[2-((S)-2-{7-[bis-(3-methyl-butyl)-amino]-5-chloro-1H-indol-2-yl}-pyrrolidin-1-yl)-acetyl]-guanidine

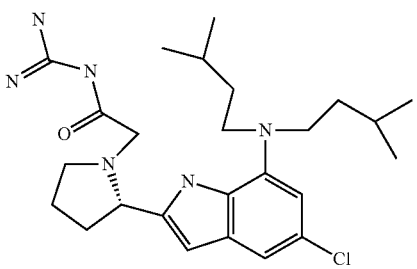

N-[2-((S)-2-{7-[Bis-(3methyl-butyl)-amino]-5-chloro-1H-indol-2-yl}-pyrrolidin-1-yl)-acetyl]-guanidine Step A: ((S)-2-{7[bis-(3-methyl-butyl)-amino]-5-chloro-1H-indol-2-yl}-pyrrolidin-1-yl)-acetic acid methyl ester (S)-2-{7-[Bis-(3-methyl-butyl)-amino]-5-chloro-1H-indol-2-yl}-pyrrolidine (60 mg, 0.16 mmol) obtained in Example 38 was dissolved in DMF (2 ml), to which were added triethylamine (18 mg, 0.16 mmol) and chloromethylacetate (18 mg, 0.16 mmol), and the mixture was stirred at 25° C. for 12 hours. The reaction was terminated by sodium bicarbonate, the reactant was extracted with ethylacetate, and the resulting organic material was dried with anhydrous magnesium sulfate. The solvent was removed under reduced pressure, and the reactant was isolated by prep TLC to give the title compound (55 mg, Yield 77%).

Step B: ((S)-2-{7-[Bis-(3-methyl-butyl)-amino]-5-chloro-1H-indol-2-yl}-pyrrolidin-1-yl)-acetic acid ((S)-2-{7-[Bis-(3-methyl-butyl)-amino]-5-chloro-1H-indol-2-yl}-pyrrolidin-1-yl)-acetic acid methyl ester (53 mg, 0.118 mmol) obtained in Step A was dissolved in methanol (1 ml), sodium methoxide (4 mg, 0.177 mmol) was added thereto, and the mixture was stirred at 25° C. for 12 hours. After completion of the reaction, the solvent was removed under reduced pressure, and the reactant was purified by prep TLC to give the title compound (41.9 mg, Yield 82%).

Step C: N-[2-((S)-2-{7-[Bis-(3-methyl-butyl)-amino]-5-chloro-1H-indol-2-yl}-pyrrolidin-1-yl)-acetyl]-guanidine ((S)-2-{7-[Bis-(3-methyl-butyl)-amino]-5-chloro-1H-indol-2-yl}-pyrrolidin-1-yl)-acetic acid obtained in Step B and guanidine HCl salt were reacted according to Step A of Example 30 to give the title compound.
MS[M+1]=475(M+1)

Examples 48 to 54

The indole compounds obtained in Preparation Examples 13 and 14, and commercially available carbonyl compound were reacted according to Steps D and E of Example 1 and Step B of Example 2 sequentially to give the compounds in the following table.

| Example | R8 | R1 | R2 | R3 | Mass |
|---|---|---|---|---|---|
| 48 | H | H | cyclopentyl | Cl | 318 |
| 49 | H | H | tetrahydropyran-4-yl | Cl | 334 |
| 50 | H | H | cyclopentyl | Me | 298 |
| 51 | acetyl | H | cyclopentyl | Me | 340 |
| 52 | H | H | tetrahydropyran-4-yl | Me | 314 |
| 53 | H | tetrahydropyran-4-yl | tetrahydropyran-4-yl | Me | 398 |
| 54 | acetyl | H | tetrahydropyran-4-yl | Me | 356 |

Example 55

[5-(1,1-Dioxo-thiomorpholin-4-ylmethyl)-2-piperidin-4-yl-1H-indol-7-yl]-(tetrahydropyran-4-yl)-amine Step A: 2-(1-t-Butoxycarbonyl-piperidin-4-yl)-7-nitro-1H-indol-5-carboxylic acid 2-(1-t-Butoxycarbonyl-piperidin-4-yl)-7-nitro-1H-indol-5-carboxylic acid ethyl ester (230 mg, 0.55 mmol) obtained in Preparation Example 15 was dissolved in a mixture solution of THF (3 ml), MeOH (3 ml) and water (3 ml), and 1N NaOH (2 ml) was added thereto, and the mixture was stirred at room temperature for 18 hours. After completion of the reaction, 0.5 N HCl (6 ml) and water (20 ml) were added thereto in order to recrystallize, and the reactant was filtered to give the title compound (196 mg, Yield 91%).
MS[M+1]=390(M+1)

Step B: 4-(5-Hydroxymethyl-7-nitro-1H-indol-2-yl)-piperidin-1-carboxylic acid t-butyl ester 2-(1-t-Butoxycarbonyl-piperidin-4-yl)-7-nitro-1H-indol-5-carboxylic acid (196 mg, 0.50 mmol) obtained in Step A was dissolved in THF (15 ml), N-methylmorpholine (52.8 mg, 0.52 mmol) and isobutylchloroformate (71.3 mg, 0.52 mmol) were added thereto at −15° C., and the mixture was stirred for 15 minutes. After completion of the reaction, sodium borohydride (59.5 mg, 1.57 mmol) was added to the reactant, and methanol (2 ml) was slowly added thereto, and then the mixture was stirred for 1 hour. After completion of the reaction, 1 N hydrochloric acid solution was added thereto, the reactant was extracted with ethyl acetate, and the resulting organic material was dried with anhydrous magnesium sulfate. The solvent was removed from the filtrate under reduced pressure, and the residue was purified by column chromatography to give the title compound (85 mg, Yield 45%).
MS[M+1]=376(M+1)

Step C: 4-[5-(1,1-Dioxo-thiomorpholin-4-ylmethyl)-7-nitro-1H-indol-2-yl)-piperidin-1-carboxylic acid t-butyl ester 4-(5-Hydroxymethyl-7-nitro-1H-indol-2-yl)-piperidin-1-carboxylic acid t-butyl ester (85 mg, 0.22 mmol) obtained in Step B was dissolved in THF (10 ml), to which were added 1,1-dioxo-thiomorpholin (90 mg, 0.67 mmol) and triphenylphosphine (119 mg, 0.45 mmol), iodine (115 mg, 0.45 mmol) was added thereto, and the mixture was stirred for 2 hours. After completion of the reaction, sodium bicarbonate solution was added thereto, the reactant was extracted with ethylacetate, and the resulting organic material was dried with anhydrous magnesium sulfate. The solvent was removed from the filtrate under reduced pressure, and the residue was purified by column chromatography to give the title compound (49 mg, Yield 44%).
MS[M+1]=493(M+1)

Step D: [5-(1,1-Dioxo-thiomorpholin-4-ylmethyl)-2-piperidin-4-yl-1H-indol-7-yl]-(tetrahydropyran-4-yl)-amine 4-[5-(1,1-Dioxo-thiomorpholin-4-ylmethyl)-7-nitro-1H-indol-2-yl)-piperidin-1-carboxylic acid t-butyl ester obtained in Step C and tetrahydropyran-4-one were reacted according to Steps D and E of Example 1, and Step B of Example 2 to give the title compound.
MS[M+1]=461(M+1)

Example 56

1-{4-[5-(1,1-Dioxo-thiomorpholin-4-ylmethyl)-7-(tetrahydropyran-4-ylamino)-1H-indol-2-yl]-piperidin-1-yl}-ethanone

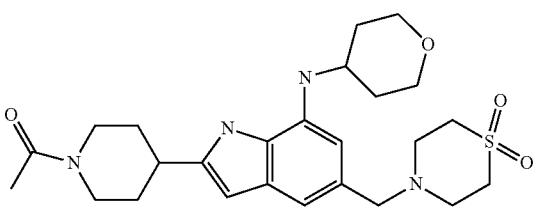

1-{4-[5-(1,1-Dioxo-1lambda*6*-thiomorpholin-4-ylmethyl)-7-(tetrahydropyran-4-ylamino)-1H-indol-2-yl]-piperidin-1-yl}-ethanone

[5-(1,1-Dioxo-thiomorpholin-4-ylmethyl)-2-piperidin-4-yl-1H-indol-7-yl]-(tetrahydropyran-4-yl)-amine obtained in Example 55 and acetic anhydride were reacted according to Example 3 to give the title compound.
MS[M+1]=489(M+1)

Example 57

(2-Cyclohexyl-5-methyl-1H-indol-7-yl)-cyclopentyl-amine

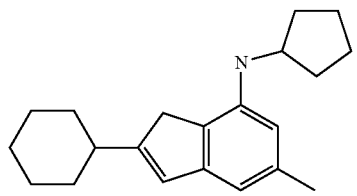

(2-Cyclohexyl-5-methyl-1H-indol-7-yl)-cyclopentyl-amine

2-Cyclohexyl-5-methyl-7-nitro-1H-indole obtained in Preparation Example 22 and cyclopentanone were reacted in the same manner as in Steps D and E of Example 1 to give the title compound.
MS[M+1]=297(M+1)

Experimental Example 1

Measurements and Analysis of the Example Compounds for the Hepatocyte Protective Effect Against the Substances Causing Hepatocyte Toxicity Various endogenous/exogenous attacks on cells trigger the mechanisms of cell death which is broadly classified into two types—i.e., apoptosis or necrosis. Using these cell death mechanisms, in the present experimental example, primary hepatocytes isolated from rats were treated with drugs which were clinically shown to result in serious side-effects of hepatocyte toxicity or various chemicals which derive cell death, and the compounds synthesized in the Examples were estimated for their hepatocyte protective effects, after 24-48 hours. The substances used to cause hepatocyte death include $CCl_4$, ActD, $H_2O_2$, doxorubicin, anti-Fas Ab/Actinomycin D, acetaminophen, EtOH, $CdCl_2$, palmitate, stearate, cyclophosphamide, terfenadine, diclofenac, simvastatin, and adefovir. Primary hepatocytes were isolated using the method of Seglen P O (Experimental Cell Research 74 (1972), pp. 450-454). Briefly, hepatocytes were isolated according to the two-step collagenase perfusion method, and dead cells were removed by low speed (500 rpm) centrifugation for 10 min using percoll gradient (Kreamer B L et al., In Vitro Cellular & Developmental Biology 22 (1986), pp. 201-211). During this step, the viability of cells was maintained 90% or above. The cells were suspended in HepatoZYME media (Gibco BRL), and the number of cells was counted. $1.5 \times 10^4$ cells in 100 μl were placed into the collagen-coated 96-well plate (BD Biocoat), and adhered on the bottom for 3-4 hours.

In order to assess the hepatocyte protective effect, the above adhered cells were pretreated with the Example compounds for 30 min. At this time, the concentration of the Example compounds was serially diluted by 2-fold or 3-fold over 5 steps starting from 30 μM, 10 μM or 1 μM depending on the experiments, and the final concentration of DMSO was adjusted to 0.2%. 30 min after the treatment by the compounds, the cells were treated by the substances causing hepatocyte death or hepatotoxic drugs at the concentrations indicated in Table 1. After 24-48 hours, the viability of cells was determined to estimate the hepatocyte protective effect. The viability of cells was determined using the WST-1 (MK-400, Takeda) method by the absorbance at 440 nm. Hepatocyte protective effects of the Example compounds were represented by "$EC_{50}$" which was calculated from measured values. "$EC_{50}$" herein means the concentration of the compound at which 50% of maximum protective effect is observed in the experiment.

Preferably, $EC_{50}$ of the Example compound is 30 μM or less, more preferably, 10 μM or less, and especially preferably, 1.0 μM or less. Table 1 shows $EC_{50}$ of the representative Example compounds against doxorubicin treatment.

TABLE 1

| Example | $EC_{50}$ (μM) | Example | $EC_{50}$ (μM) | Example | $EC_{50}$ (μM) |
| --- | --- | --- | --- | --- | --- |
| 1 | 0.16 | 3 | 0.27 | 7 | 0.44 |
| 8 | 0.24 | 9 | 0.25 | 12 | 0.6 |
| 13 | 1.8 | 14 | 0.30 | 18 | 0.24 |
| 19 | 0.27 | 22 | 0.90 | 48 | 0.21 |

Experimental Example 2

Protective Effects when tBHP (tert-Butyl Hydroxy Peroxide; t-BuOOH) was Treated on Hepatocytes and Other Cells Derived from Various Tissues 1) Protective Effect when tBHP was Treated on Primary Hepatocytes Hepatocytes were isolated according to the same procedure as Experimental Example 1, suspended in DMEM (Gibco+10% FBS+1× antibiotics) media, and distributed to the plate. After 24 h from the distribution of hepatocytes, the compounds were serially diluted by 3-fold to the final concentration of 30, 10, 3, 1, 0.3, 0.1 μM, by which the cells were pretreated for 30 min. Cells were treated with tBHP at the final concentration of 300 μM, and the protective effects were determined after 1 hour. As in Experimental Example 1, after the treatment with WST-1 (Takeda, 10 μl) for 1.5 hours, $EC_{50}$ values were calculated by absorbance measurements at 440 nm using SpectraMax (Molecular Device).

2) Protective Effect when tBHP was Treated on Pancreatic Cells (Linm5F)

In order to determine the protective effect on pancreatic cells, Linm5F cells, a sort of the beta cells, were plated into a 96-well plate in the amount of $2\times10^4$ cells/well, and incubated for 24 hours. The Example compounds were serially diluted by 3-fold to the final concentration of 30, 10, 3, 1, 0.3 and 0.1 μM, by which each well was treated for 1 hour. Cells were treated with tBHP at the final concentration of 400 μM, and further incubated for 5 hours. Protective effects were determined using the SRB (Sulforhodamine B Protein) method in which the total amount of cellular protein is stained. Briefly, cells were incubated for 5 hours, 50 μl of 4% formaldehyde solution was added to each well to fix the cells, and stored for about 30 min at room temperature. After discarding the media, each well was washed with distilled water 2-3 times, and the plate was dried in an oven at 50° C. 50 μl of SRB solution was added to each well, and the plate was placed for about 30 min at room temperature. After removing SRB solution, the plate was washed with 1% acetic acid solution 2-3 times. After drying the plate in an oven at 50° C., 100 μl of 10 mM Tris was added to elute SRB which was staining the intracellular protein. Absorbance was measured at 590 nm and 650 nm using SpectraMax, and the absorbance at 650 nm was subtracted from the absorbance at 590 nm to calculate the $EC_{50}$ value.

3) Protective Effect when tBHP was Treated on Cardiac Cells (H9C2, White Rat Cardiomyocyte)

In order to assess the protective effect on cardiac cells, H9C2 cells were plated in the amount of $1.5\times10^4$ cells/well, and incubated for 24 hours. The Example compounds were serially diluted by 3-fold to the final concentrations of 30, 10, 3, 1, 0.3 and 0.1 μM, by which each well was treated for 45 min. Cells were treated with tBHP at the final concentration of 400 μM, and incubated for 2 hours. The protective effect of each compound was determined using the same SRB method as in Linm5F of above mentioned 2).

4) Protective Effect when tBHP was Treated on Kidney Cells (LLC-PK1)

In order to determine the protective effect on kidney cells, $4\times10^4$ cells were distributed into each well, and incubated for 24 hours. Cells were treated with the Example compounds at the final concentration of 30, 10, 3, 1, 0.3 and 0.1 μM, and incubated for 30 min. Cells were treated with 400 μM tBHP, and further incubated for 6 hours. The protective effect of each compound was determined using the same SRB method as in Linm5F of the above-mentioned 2).

5) Protective Effect when tBHP was Treated on Chondrocytes

In order to determine the protective effect on chondrocytes, chondrocytes were isolated from the 2 hind legs of 16 week-old SD rats (body weight: 450-460 g). The isolation method was as follows. Cartilage isolated from the knee regions of rat hind legs was transferred to a 100 pi plate containing PBS (+1× antibiotics). PBS was maintained at 4° C. in an ice bath. PBS was exchanged with a fresh one and centrifuged at 1,000 rpm. After removal of PBS, 3 ml of 1× trypsin (Gibco) at the temperature of 37° C. was added and followed by treatment for 15 min. Supernatant was discarded after centrifugation and washed again with PBS. Supernatant was discarded after centrifugation. After the addition of 0.2% collagenase (Worthington, type II) thereto, the cells were isolated by the overnight incubation in a rotating 37° C. incubator. The filtered cell solution was centrifuged, and the supernatant was discarded. Following the washing with PBS, cells were suspended in 10 ml of DMEM/F-12 (Gibco, 10% FBS). $2\times10^4$ cells were distributed to each well and incubated for 24 hours. The Example compounds were serially diluted by 3-fold to the final concentrations of 30, 10, 3, 1, 0.3 and 0.1 μM, by which each well was treated for 1 hour. Cells were treated with tBHP at the final concentration of 500 μM and incubated for 3 hours. The protective effect of each compound was determined using the same SRB staining method as in Linm5F of the above-mentioned 2).

6) Protective Effect when tBHP was Treated on Brain Cells (SK-N-MC)

In order to assess the protective effect on brain cells, $2\times10^4$ brain cells were distributed into a 96-well plate using DMEM media (Gibco, 10% FBS), and incubated for 24 hours. The Example compounds were serially diluted by 3-fold to the final concentrations of 30, 10, 3, 1, 0.3 and 0.1 μM, by which each well was treated for 1 hour. Cells were treated with tBHP at the final concentration of 400 μM and incubated for 6 hours. 50 μl of media was taken from each well to proceed with LDH assay (Promega), In the LDH assay, 50 μl of media was mixed with 50 μl of assay solution.

After reaction for 30 min at room temperature, absorbance was measured at 490 nm using SpectraMax (Molecular Device).

INDUSTRIAL APPLICABILITY

As is demonstrated in above results, the novel compound according to the present invention not only exhibits the effects for hepatoprotection and hepatic functional improvement, but also can be useful for the prevention and treatment of chronic hepatic diseases such as fatty liver, hepatic fibrosis, hepatocirrhosis, etc. and acute/chronic hepatic diseases such as hepatitis, etc. caused by virus or drugs. The compound of the present invention also exhibits the necrosis inhibitory efficacy in cells from the pancreas, kidney, brain, cartilage, and heart.

Therefore, the compound of the present invention can be useful in the prevention and treatment of necrosis and associated diseases.

It would be within the ability of those skilled in the art to conduct various applications and modifications without departing from the scope of the present invention.

The invention claimed is:

1. An indole compound of the following Formula (1) or a pharmaceutically acceptable salt or isomer thereof, wherein the isomer is an R or S isomer, a racemate, a mixture of diastereomers, or an individual diastereomer:

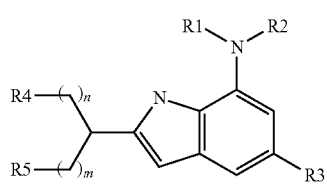

(1)

in which
m denotes a number of 1 to 3;
n denotes a number of 0 to 2;
R1 represents hydrogen, $C_1$-$C_6$-alkyl, —$(CH_2)_n$—$C_3$-$C_6$-cycloalkyl or —$(CH_2)_n$-heterocyclyl, wherein heterocyclyl is a 4- to 8-membered ring having 1 to 3 heteroatoms selected from N, O and S;
R2 represents $C_1$-$C_6$-alkyl or —$(CH_2)_n$-A-R6, wherein A represents $C_4$-$C_8$-cycloalkyl, or represents 4- to 8-membered heterocyclyl or heteroaryl each of which has 1 to 3 heteroatoms selected from N, O and S, or represents 6- to 10-membered aryl, R6 represents hydrogen, $C_1$-$C_6$-alkyl, halogen, hydroxy, nitrile, nitro, —C(O)—R7 or —$SO_2$R7, and R7 represents $C_1$-$C_6$-alkyl or allyl, or represents 6- to 10-membered aryl, or represents 4- to 8-membered heterocyclyl or heteroaryl each of which has 1 to 3 heteroatoms selected from N and S, and is optionally substituted with oxo;
R3 represents hydrogen, halogen, hydroxy, —O—R7, —NH—R7 or —$(CH_2)_n$—R7;
R4 represents hydrogen or XR8R9, wherein X represents CH or N, R8 and R9 independently of one another represent hydrogen or Z—R10, Z represents —$(CH_2)_n$—, —C(O)—, —C(O)($CH_2)_n$— or —$(CH_2)_n$C(O)—, R10 represents hydrogen, amino, $C_3$-$C_6$-cycloalkyl or —$(NH)_rC(=NH)NH_2$, or represents 4- to 8-membered heteroaryl or heterocyclyl each of which has 1 to 3 heteroatoms selected from N, O and S, and r denotes a number of 0 or 1;

R5 represents hydroxy or 6- to 10-membered aryl, or represents —$(CH_2)_n$-4- to 9-membered heterocyclyl which has 1 to 4 heteroatoms selected from N, O and S, and optionally contains oxo; and
where alkyl, alkoxy, aryl, cycloalkyl, heterocycle and heteroaryl may be optionally substituted, and the substituents are one or more selected from the group consisting of hydroxy, halogen, nitrile, amino, $C_1$-$C_6$-alkylamino, di($C_1$-$C_6$-alkyl)amino, carboxy, $C_1$-$C_6$-alkyl, halogeno-$C_1$-$C_6$-alkyl, $C_1$-$C_6$-alkoxy, aryl-$C_1$-$C_6$-alkoxy and oxo.

2. The compound according to claim 1, wherein
m denotes a number of 1 to 3;
n denotes a number of 0 to 2;
R1 represents hydrogen, $C_1$-$C_6$-alkyl, —$(CH_2)_n$—$C_3$-$C_6$-cycloalkyl or —$(CH_2)_n$-heterocyclyl, wherein heterocyclyl is a 4- to 8-membered ring having 1 to 3 heteroatoms selected from N, O and S;
R2 represents $C_1$-$C_6$-alkyl or —$(CH_2)_n$-A-R6, wherein A represents $C_4$-$C_6$-cycloalkyl, or represents 5- or 6-membered heterocyclyl or heteroaryl each of which has 1 to 3 heteroatoms selected from N, O and S, or represents 6- to 10-membered aryl, R6 represents hydrogen, $C_1$-$C_6$-alkyl, halogen, hydroxy, —C(O)—R7 or —$SO_2$R7, and R7 represents $C_1$-$C_6$-alkyl, or represents 6- to 10-membered aryl, or represents 5- or 6-membered heterocyclyl or heteroaryl each of which has 1 to 3 heteroatoms selected from N and S, and is optionally substituted with oxo;
R3 represents hydrogen, halogen, —O—R7, —NH—R7 or —$(CH_2)_n$—R7;
R4 represents hydrogen or XR8R9, wherein X represents CH or N, R8 and R9 independently of one another represent hydrogen or Z—R10, Z represents —$(CH_2)_n$—, —C(O)—, —C(O)($CH_2)_n$— or —$(CH_2)_n$C(O)—, R10 represents hydrogen, amino, $C_3$-$C_6$-cycloalkyl or —$(NH)_rC(=NH)NH_2$, or represents 4- to 8-membered heteroaryl or heterocyclyl each of which has 1 to 3 heteroatoms selected from N, O and S, and is optionally substituted with amino, and r denotes a number of 0 or 1; and
R5 represents hydroxy or 6- to 10-membered aryl, or represents —$(CH_2)_n$-4- to 9-membered heterocyclyl which has 1 to 4 heteroatoms selected from N, O and S, and optionally contains oxo and is optionally substituted with halogeno-$C_1$-$C_6$-alkyl.

3. The compound according to claim 1, which is the following Formula (1a):

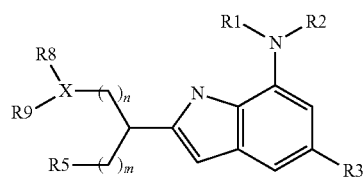

(1a)

wherein X, m, n, R1, R2, R3, R5, R8 and R9 are the same as defined in claim 1.

4. The compound according to claim 1, wherein R1 is hydrogen, $C_1$-$C_6$-alkyl or 5- or 6-membered heterocyclyl having 1 to 3 heteroatoms selected from N, O and S.

5. The compound according to claim 4, wherein R1 is hydrogen, isopentyl or tetrahydropyran.

6. The compound according to claim 1, wherein R2 is $C_1$-$C_6$-alkyl or —$(CH_2)_n$-A-R6, wherein n denotes a number of 0 to 2, A represents $C_4$-$C_6$-cycloalkyl, or represents 5- or 6-membered heterocyclyl having 1 or 2 heteroatoms selected from N and O, or represents phenyl, R6 represents hydrogen, —C(O)—R7 or —$SO_2$R7, and R7 represents $C_1$-$C_3$-alkyl.

7. The compound according to claim 6, wherein R2 is isopentyl, cyclopentyl, benzyl, tetrahydropyran, tetrahydropyran-4-ylmethyl, 1-acetyl-piperidine, tetrahydropyran-2-ylmethyl or piperidin-4-ylmethyl.

8. The compound according to claim 1, wherein R3 is hydrogen, halogen or —$(CH_2)_n$—R7, wherein n denotes a number of 0 to 2, R7 represents $C_1$-$C_6$-alkyl, or represents 5- or 6-membered heterocyclyl which has 1 or 2 heteroatoms selected from N and S, and is optionally substituted with oxo.

9. The compound according to claim 8, wherein R3 is hydrogen, methyl, chloro or 1,1-dioxothiomorpholin-4-yl-methyl.

10. The compound according to claim 1, wherein R5 is hydroxyl, 6- to 10-membered aryl or —$(CH_2)_n$-4- to 9-membered heterocyclyl which has 1 to 4 heteroatoms selected from N, O and S, and optionally contains oxo and is optionally substituted with halogeno-$C_1$-$C_3$-alkyl, wherein n denotes a number of 0 to 2.

11. The compound according to claim 10, wherein R5 is hydroxy, 1,1-dioxothiomorpholine, 2-oxopiperazine, 3-trifluoromethyl-5,6,7,8-tetrahydro-[1,2,4]triazolo[4,3-a]pyrazin-1-yl, morpholine or phenyl.

12. The compound according to claim 1, wherein R8 is hydrogen or Z—R10, wherein Z represents —$(CH_2)_n$—, —C(O)—, —C(O)$(CH_2)_n$— or —$(CH_2)_n$C(O)—, n denotes a number of 0 to 2, R10 represents hydrogen, amino, $C_4$-$C_6$-cycloalkyl or —$(NH)_rC(=NH)NH_2$, or represents 5- or 6-membered heteroaryl or heterocyclyl each of which has 1 to 3 heteroatoms selected from N and S, and is optionally substituted with amino, and r denotes a number of 0 or 1.

13. The compound according to claim 1, wherein R8 is hydrogen, cyclohexyl-ethyl, 2-amino-pyridin-3-ylmethyl, pyrrolidine, 3-amino-triazol-5-carbonyl, aminomethyl-carbonyl, $NH_2$(NH=)C—, $NH_2$(NH=)C—NH—$CH_2$—C(O)—, 2-amino-thiazol-4-ylmethyl, cyclopentyl-methyl, $NH_2$(NH=)C—NH—C(O)—$CH_2$— or acetyl.

14. An indole compound, which is selected from the group consisting of:
    4-(5-Chloro-7-cyclopentylamino-1H-indol-2-ylmethyl)-piperazin-2-one;
    4-{2-[5-Chloro-7-(piperidin-4-ylamino)-1H-indol-2-yl]-ethyl}-piperazin-2-one;
    4-{2-[7-(1-Acetyl-piperidin-4-ylamino)-5-chloro-1H-indol-2-yl]-ethyl}-piperazin-2-one;
    (5-Chloro-7-cyclopentylamino-1H-indol-2-yl)-methanol;
    2-(5-Chloro-7-cyclopentylamino-1H-indol-2-yl)-ethanol;
    4-{5-Methyl-7-[(piperidin-4-ylmethyl)-amino]-1H-indol-2-ylmethyl}-piperazin-2-one;
    [2-(1,1-Dioxothiomorpholin-4-ylmethyl)-5-methyl-1H-indol-7-yl]-(tetrahydropyran-4-ylmethyl)-amine;
    Cyclopentyl-[2-(1,1-dioxothiomorpholin-4-ylmethyl)-5-methyl-1H-indol-7-yl]-amine;
    4-[5-Methyl-7-(tetrahydropyran-4-ylmethylamino)-1H-indol-2-ylmethyl]-piperazin-2-one;
    {5-Chloro-2-[2-(3-trifluoromethyl-5,6,7,8-tetrahydro-[1,2,4]triazolo[4,3-a]pyrazin-1-yl)-ethyl]-1H-indol-7-yl}-(tetrahydrofuran-2-ylmethyl)-amine;
    {5-Chloro-2-[2-(3-trifluoromethyl-5,6,7,8-tetrahydro-[1,2,4]triazolo[4,3-a]pyrazin-1-yl)-ethyl]-1H-indol-7-yl}-(tetrahydropyran-2-ylmethyl)-amine;
    {5-Chloro-2-[2-(3-trifluoromethyl-5,6,7,8-tetrahydro-[1,2,4]triazolo[4,3-a]pyrazin-1-yl)-ethyl]-1H-indol-7-yl}-(1-methanesulfonyl-piperidin-4-yl)-amine;
    1-(4-{5-Chloro-2-[2-(3-trifluoromethyl-5,6,7,8-tetrahydro-[1,2,4]triazolo[4,3-a]pyrazin-1-yl)-ethyl]-1H-indol-7-yl}-piperidin-1-yl)-ethanone;
    4-[2-(7-Benzylamino-5-chloro-1H-indol-2-yl)-ethyl]-piperazin-2-one;
    4-(2-{5-Chloro-7-[(tetrahydrofuran-2-ylmethyl)-amino]-1H-indol-2-yl}-ethyl)-piperazin-2-one;
    4-(2-{5-Chloro-7-[(tetrahydropyran-2-ylmethyl)-amino]-1H-indol-2-yl}-ethyl)-piperazin-2-one;
    4-{5-Chloro-7-[(tetrahydropyran-4-ylmethyl)-amino]-1H-indol-2-ylmethyl}-piperazin-2-one;
    {5-Chloro-2-[2-(1,1-dioxothiomorpholin-4-yl)-ethyl]-1H-indol-7-yl}-(tetrahydropyran-4-yl)-amine;
    {5-Chloro-2-[2-(1,1-dioxothiomorpholin-4-yl)-ethyl]-1H-indol-7-yl}-cyclopentyl-amine;
    {5-Chloro-2-[2-(3-trifluoromethyl-5,6,7,8-tetrahydro-[1,2,4]triazolo[4,3-a]pyrazin-1-yl)-ethyl]-1H-indol-7-yl}-cyclopentyl-amine;
    {5-Chloro-2-[2-(1,1-dioxothiomorpholin-4-yl)-ethyl]-1H-indol-7-yl}-(tetrahydropyran-4-ylmethyl)-amine;
    4-(2-{5-Chloro-7-[(tetrahydropyran-4-ylmethyl)-amino]-1H-indol-2-yl}-ethyl)-piperazin-2-one;
    {5-Chloro-2-[2-(3-trifluoromethyl-5,6,7,8-tetrahydro-[1,2,4]triazolo[4,3-a]pyrazin-1-yl)-ethyl]-1H-indol-7-yl}-(tetrahydropyran-4-ylmethyl)-amine;
    [5-Chloro-2-(2-morpholin-4-yl-ethyl)-1H-indol-7-yl-(tetrahydropyran-4-ylmethyl)-amine;
    Cyclopentyl-(5-methyl-2-morpholin-4-ylmethyl-1H-indol-7-yl)-amine;
    [2-((R)-1-amino-2-phenyl-ethyl)-5-methyl-1H-indol-7-yl]-cyclopentyl-amine;
    {2-[(R)-1-(2-cyclohexyl-ethylamino)-2-phenyl-ethyl]-5-methyl-1H-indol-7-yl}-cyclopentylamine;
    Benzyl-{5-chloro-2-[(R)-2-phenyl-1-(pyrrolidin-3-ylamino)-ethyl]-1H-indol-7-yl}-amine;
    2-Amino-N-[(R)-1-(7-benzylamino-5-chloro-1H-indol-2-yl)-2-phenylethyl]-acetamide;
    N-[(R)-1-(7-Benzylamino-5-chloro-1H-indol-2-yl)-2-phenyl-ethyl]-guanidine;
    {2-[(R)-1-(cyclohexylmethyl-amino)-2-phenyl-ethyl]-5-methyl-1H-indol-7-yl}-cyclopentyl-amine;
    (2-{(S)-1-[(2-amino-pyridin-3-ylmethyl)-amino]-2-phenyl-ethyl}-5-chloro-1H-indol-7-yl)-(3-methyl-butyl)-amine;
    3-Amino-4H-[1,2,4]triazol-4-carboxilic acid [(S)-1-(7-benzylamino-5-chloro-1H-indol-2-yl)-2-phenyl-ethyl]-amide;
    2-Amino-N-{(S)-1-[5-chloro-7-(3-methyl-butylamino)-1H-indol-2-yl]-2-phenyl-ethyl}-acetamide;
    N-[(R)-1-(7-benzylamino-5-chloro-1H-indol-2-yl)-2-phenyl-ethyl]-2-guanidino-acetamide; and
    (S)-2-Amino-2-(5-chloro-7-cyclopentylamino-1H-indol-2-yl)-ethanol;

or a pharmaceutically acceptable salt or isomer thereof, wherein the isomer is an R or S isomer, a racemate, a mixture of diastereomers, or an individual diastereomer.

15. A method of preparing a composition for the prevention or treatment of necrosis and necrosis-associated diseases, which comprises the step of mixing the compound of Formula (1), a pharmaceutically acceptable salt or isomer thereof as defined in claim 1 as an active ingredient together with a pharmaceutically acceptable carrier.

16. A composition comprising a therapeutically effective amount of the compound of Formula (1), a pharmaceutically acceptable salt or isomer thereof as defined in claim 1 as an active ingredient together with a pharmaceutically acceptable carrier or diluent.

\* \* \* \* \*